US008709405B2

(12) United States Patent
Coggin, Jr. et al.

(10) Patent No.: US 8,709,405 B2
(45) Date of Patent: *Apr. 29, 2014

(54) CANCER VACCINES CONTAINING EPITOPES OF ONCOFETAL ANTIGEN

(75) Inventors: Joseph H. Coggin, Jr., Mobile, AL (US); James W. Rohrer, Wilmer, AL (US); Adel L. Barsoum, Mobile, AL (US)

(73) Assignee: South Alabama Medical Science Foundation, Mobile, AL (US)

( * ) Notice: Subject to any disclaimer, the term of this patent is extended or adjusted under 35 U.S.C. 154(b) by 164 days.

This patent is subject to a terminal disclaimer.

(21) Appl. No.: 12/462,514

(22) Filed: Aug. 5, 2009

(65) Prior Publication Data

US 2010/0183643 A1  Jul. 22, 2010

Related U.S. Application Data

(63) Continuation of application No. 10/523,277, filed as application No. PCT/US03/24518 on Aug. 4, 2003, now Pat. No. 7,718,762.

(60) Provisional application No. 60/400,851, filed on Aug. 2, 2002.

(51) Int. Cl.
*A61K 35/12* (2006.01)
*C12N 5/0784* (2010.01)

(52) U.S. Cl.
USPC ............... 424/93.71; 424/278.1; 435/375; 435/377

(58) Field of Classification Search
None
See application file for complete search history.

(56) References Cited

U.S. PATENT DOCUMENTS

| | | | |
|---|---|---|---|
| 6,080,725 A | 6/2000 | Marciani | |
| 6,335,174 B1 | 1/2002 | Rohrer et al. | |
| 6,602,510 B1 | 8/2003 | Fikes et al. | |
| 2003/0152555 A1* | 8/2003 | Liu et al. ............. | 424/93.7 |
| 2004/0001847 A1 | 1/2004 | Lasalvia-Prisco | |
| 2004/0253574 A1 | 12/2004 | Schuler et al. | |
| 2009/0041794 A1 | 2/2009 | Zeis | |

FOREIGN PATENT DOCUMENTS

| | | |
|---|---|---|
| WO | 9738089 | 10/1997 |
| WO | WO 98/53048 | * 11/1998 |

OTHER PUBLICATIONS

Morse et al (Clinical Cancer Research, 1999, vol. 5, pp. 1331-1338).*
Mutis et al (PNAS, 1994, vol. 91, pp. 9456-9460).*
Rohrer, J. W., et al., Mod. Asp. Immunobiol. 1:191 (2001).
Rohrer, J. W., et al., Mod. Asp. Immunobiol. 16: 27-34 (2005).
Nukaya et al, Identification of the HLA-A24 Epitope Peptides of Carcinoembryonic Antigen Which Induce Tumor-Reactive Cytoxic T Lymphocyte. Int. J. Cancer, Jan. 1999, vol. 80, No. 1, pp. 92-97.
Coggin Jr. et al, 37 KiloDalton Oncofetal Antigen Protein and Immature Laminin Receptor Protein are Identical, Universal T-Cell Indicing Immunogenes on Primary Rodent and Human Cancers. Anticancer Res.. Nov.-Dec. 1999. vol. 19, No. 6C, pp. 5535-5542.
Armstrong et al, Vaccines in Oncoloogy: Background and Clinical Potential, British Journal of Radiology. Nov. 2001, vol. 74, No. 887, pp. 991-1002.
Irie RF et al (J. Natl. Cancer Inst. 1979; 63(2):367-373).
Rohrer JW et al (J. Immunol. 1999; 162(11):6880-6892).
Oseroff et al (Vaccine 1999; 16(8):823-833).
Rohrer et al., Journal of Immunology; 176; 2844-2856 (2006).
Tai et al, Proc. Natl. Acad. Sci., 80:5392-5396 (Sep. 1983).
Rohrer & Coggin, Journal of Immunology, The Williams and Wilkins Co. Baltimore, US, 155 (12); 5719-5727 (1995).
Zelle-Rieser et al: Journal of Urology, Baltimore. MD, US., 165(5); 1705-1709 (2001).
Astrow, A. B., Lancet 343:494 (1994).
Bailar J. C., et al., N. Engl. J. Med. 314:1226 (1986).
Gallagher, H. S., et al., Cancer 23:855 (1969).
Spratt, J. S., et al., Cancer Res. 46:970 (1986).
Zhuang, A., et al., Cancer Res. 55:467 (1995).
Leffett, M. S., et al., Cancer Res. 37:4112 (1977).
Coggin, J. H., Jr., Mol. Biother. 1:223 (1989).
Van den Eynde, B. J., et al., Curr. Opinion Immunol. 9:684 (1997).
Melief, C., et al., Immunol. Rev. 145:167 (1995).
Greenberg, P. D., et al., Adv. Immunol. 49:281 (1991).
Coulie, P. G., et al., J. Immunother. 14:104 (1993).
Hellstrom, I., et al., Crit. Rev. Immunol. 18:1 (1998).
Nabeta, Y. Mod., Asp. Immunobiol. 1:17 (2000).
Coggin, J. H., Jr., et al., Immunol. Today 19:405 (1998).
Seiter, S., et al., Mod. Asp. Immunobiol. 1:121 (2000).
Landowski, T. H., et al., Biochem. 34:11276 (1995).
Castronovo, V., Invasion Metastasis 13:1 (1993).
van den Brule, F. A., et al., Biochem Biophys. Res. Commun. 201:388 (1994).
Menard, S., et al., Biochem. 67:155 (1997).
Coggin, J. H., Jr., et al., Anticancer Res. 19:1 (1999).
Liotta, L. A., et al., Prog. Clin. Biol. Res. 256:3 (1988).
Azavoorian, S., et al., Cancer 71:1368 (1993).
Terranova, V. P., et al., Cancer Res. 42:2261 (1982).
Terranova, V. P., et al., Science 226:982 (1984).
Ardini, E., et al., J. Biol. Chem. 272:2342 (1997).
Romanov, V., et al., Cell Adhes. Commun. 2:201 (1994).
Turpeeniemi, H. T., et al., J. Biol. Chem. 261:1883 (1986).
Sweeney, T. M., et al., Cancer Metastasis Rev. 10:245 (1991).
D'Erico, A. S., et al., Mol. Pathol. 4:239 (1991).
Monteagudo, C. M., et al., Am. J. Pathol. 136:585 (1990).
Grigoni, W. F., et al., Am. J. Pathol. 138:647 (1991).
Sobel, M. E., Semin. Cancer Biol. 4:311 (1993).
Martignone, S., et al., J. Natl. Cancer Inst. 85:398 (1993).
Waltregny, D., et al., J. Natl. Cancer Inst. 89:1224 (1997).
Pellegrini, R., et al., Breast Cancer Res. Treat. 35:195 (1995).
Menard, S., et al., Br. J. Cancer 69:1126 (1994).
Vollmers, H. P., et al., Febs Letters 172:17 (1984).
Wu, S. Chung-hua Ping Li Hsueh Tsa Chih 22:207 (1993).
Terranova, V. P., et al., Cancer Res. 42:2265 (1982).
Rohrer, J. W., et al., J. Immunol. 154:2266 (1995).

(Continued)

*Primary Examiner* — Karen Canella
(74) *Attorney, Agent, or Firm* — Lerner, David, Littenberg, Krumholz & Mentlik, LLP

(57) ABSTRACT

Disclosed are fragments of oncofetal antigen, otherwise known as immature laminin receptor protein that specifically stimulate one T cell subclass. The fragments may be formulated into compositions for potentiating T cell-mediated responses in mammalian cancer patients. They also have therapeutic uses in vitro.

20 Claims, No Drawings

(56) References Cited

OTHER PUBLICATIONS

Coggin, J. H., Jr., et al., Am. J. Pathol. 130:136 (1988).
Coggin, J. H., Jr., et al., Int. J. Rad. Biol. 71:81 (1997).
Rohrer, J. W., et al., J. Immunol. 162:6880 (1999).
van den Brule, F. A., et al., Hum. Pathol. 27:1185 (1996).
Payne, W. J., Jr., et al., J. Natl. Cancer Inst. 75:527 (1985).
Rao, et al., Biochemistry 28:7476-7486 (1989).
Yow, et al., Proc. Natl. Acad. Sci. USA 85:6394-6398 (1988).
Coggin, et al., Arch. Otolaryngol Head Neck Surg. 119:1257-1266 (1993).
Ambrosch, et al., Vaccine 15:1209-1213 (1997).
Andrieu, et al., Eur. J. Immunol. 30:3256-65 (2000).
B. Pulendran, et al., J. Immunol 165:566-572 (2000)).
Banchereau, et al., Nature 392:245-52 (1998)).
BenMohamed, et al., Immunology 106:113-121 (2002).
BenMohamed, et al., The Lancet Infect. Dis. 2:425-31 (2002).
BenMohamed, et al., Vaccine 18:2843-55 (2000).
Boyum, Scand. J. Clin. Lab. Invest. 21:97:S77 (1968).
Chikh, et al., J. Immunol. 167:6462-6470 (2001).
Davila, E., E. Cells. 2000, J. Immunol. 165:539.
Deprez, et al., Vaccine 14:375-382 (1996).
E. Proietti, et al., J. Immunol. 169:375-383 (2002).
Gahery-Segard, et al., J. Virol. 74:1694-1703 (2000).
Vitello, et al., J. Clin. Invest. 95:341-349 (1995).
Gras-Masse, Mol. Immunol. 38:423-431(2001).
Guan, et al., Bioconjugate Chem. 9:451-458 (1998)).
Gupta, et al., Vaccine 13:1263-76 (1995).
Gursel, et al., J. Immunol. 167:3324-3328 (2001).
Hartmann, G., G. J. Weiner, A. M. Krieg. 1999, Proc. Natl. Acad. Sci. USA 96:9305.
I Krishnan, J. Immunol. 165:5177-5185 (2000)).
Janeway, C. A., P. Travers, M. Walport, and M. Shlomchik. 2001. Immunobiology: The Immune System in Health and Disease. Garland Publishing, New York, pp. 307-309.
Krieg, A. M., A. K. Yi, S. Matson, T. J. Waldschmidt, et al., Nature 374:546 (1995).
Lipford, G. B., M. Bauer, C. Blank, et al. 1997. Eur. J. Immunol. 27:2340.
Loing, et al., J. Immunol. 164:900-907 (2000).
Lynch, D. H., E. Andreasen, E. Maraskovsky, et al. 1997, Nat. Med. 3:625.
Mattei, et al., J. Immunol. 167:1179-1187 (2000).
Mattner, et al., Cancer Res. 62:1477-1480 (2002).
Mowat, Immunol. Lett. 65:133-40 (1999).
Nair, et al., Annals of Surgery 235:540-549 (2002)).
Nair, supra., Holtl, et al., Clin. Cancer Res. 8:3369-76 (2002).
Nishiguchi, et al., J. Immunol. 166:2610-16 (2001).
Ota, et al., Cancer Res. 62:1471-1476 (2002).
Pialoux, et al., AIDS 15:1239-49 (2001).
Podda, A. 2001, Vaccine 19:2673, Jun. 16, 2011.
Posnett et al., J. Biol Chem. 263:1719-1725 (1988).
Pulendran, B., J. L. Smith, G. Caspary, et al. 1999, Proc. Natl. Acad. Sci. USA 96:1036.
Pulendran, B., J. L. Smith, M. Jenkins, et al. 1998, J. Exp. Med. 188:2075.
Rosenberg, S. A., J. C. Yang, D. J. Schwartzentruber, et al., Nat. Med. 4:321 (1998).
Rouaix, et al., Vaccine 12:1209-14 (1994).
Sallusto, et al., Arthritis Res. 4 Suppl. 3:S127-132 (2002).
Schild, et al., J. Exp. Med. 174:1665-1668 (1991).
Shurin, M. R., P. P. Pandharipande, T. D. Zorina, et al. 1997. Cell. Immunol. 179:174.
Sparwasser, T., E. S. Koch, R. M. Vabulas, et al. 1998. Eur. J. Immunol. 28:2045.
Sparwasser, T., R. M. Vabulas, B. Villmow, et al. 2000, Eur. J. Immunol. 30:3591.
Suen, et al., Immunol. 106:326-335 (2002).
Tam, PNAS USA 85:5409-5413 (1988).
Tsunoda, et al., Vaccine 17:675-685 (1999).
Vabulas, R. M., H. Pircher, G. B. Lipford, et. al. 2000, J. Immunol. 164:2372.
White, et al., Vaccine 13:1111-1122 (1995).
Wysocki et al., Proc. Natl. Acad. Sci. (USA) 75:2844 (1978).
Zeng, J. Immunother. 24:195-204 (2001).
Zhou et al., Immunobiology 190:35-52 (1994).
Zhou, et al., J. Immunother 25:289-303 (2002).
International Search Report and Written Opinion, PCT/US2010/041556, dated Mar. 15, 2011.
Siegel, S. et al., Blood. 102(13) : 4416-4423 (Jul. 17, 2003).
Joseph, H. Coggin Jr. , et al., Mod. Asp. Immunobiol. 16: 27-34 (2005).
Schwaab, T., et al., Clin. Cancer Res. 15(15): 4986-4992 (Jul. 21, 2009).

* cited by examiner

SEQUENCE LISTING

```
<160> NUMBER OF SEQ ID NOS: 82

<210> SEQ ID NO 1
<211> LENGTH: 1067
<212> TYPE: DNA
<213> ORGANISM: Mus musculus
<220> FEATURE:
<221> NAME/KEY: CDS
<222> LOCATION: (86)..(970)

<400> SEQUENCE: 1
gtcgacccac gcgtccgcta cccggggacg ggtccatacg gcgttgttct tgattcccat      60
cgtaacttaa agggaaactt acaca atg tcc gga gcc ctt gac gtc ctg cag     112
                            Met Ser Gly Ala Leu Asp Val Leu Gln
                             1               5 atg aag gag gag gat gtc ctc aaa ttc ctt gct gcg gga acc cac tta     160
Met Lys Glu Glu Asp Val Leu Lys Phe Leu Ala Ala Gly Thr His Leu
 10              15                  20                  25 ggt ggc acc aac ctt gac ttt cag atg gag cag tac atc tac aaa agg     208
Gly Gly Thr Asn Leu Asp Phe Gln Met Glu Gln Tyr Ile Tyr Lys Arg
                 30                  35                  40 aaa agt gac ggt atc tac atc ata aac ctg aag agg acc tgg gag aag     256
Lys Ser Asp Gly Ile Tyr Ile Ile Asn Leu Lys Arg Thr Trp Glu Lys
             45                  50                  55 ctg ttg ctc gca gct cga gct att gtt gcc atc gag aat cct gct gac     304
Leu Leu Leu Ala Ala Arg Ala Ile Val Ala Ile Glu Asn Pro Ala Asp
         60                  65                  70 gtc agc gtc atc tcc tcc agg aac act ggc cag cga gct gtg ctg aag     352
Val Ser Val Ile Ser Ser Arg Asn Thr Gly Gln Arg Ala Val Leu Lys
     75                  80                  85 ttt gct gct gcc aca gga gcc act ccg atc gct ggc cgc ttc aca cct     400
Phe Ala Ala Ala Thr Gly Ala Thr Pro Ile Ala Gly Arg Phe Thr Pro
 90                  95                 100                 105 ggg acc ttc act aac cag atc caa gca gcc ttc agg gag cca cgg ctt     448
Gly Thr Phe Thr Asn Gln Ile Gln Ala Ala Phe Arg Glu Pro Arg Leu
                110                 115                 120 cta gtg gtg acc gat ccc agg gct gac cat cag cca ctc aca gag gcc     496
Leu Val Val Thr Asp Pro Arg Ala Asp His Gln Pro Leu Thr Glu Ala
            125                 130                 135 tct tat gtc aac ctg ccc acc att gct ctg tgt aac aca gat tct ccc     544
Ser Tyr Val Asn Leu Pro Thr Ile Ala Leu Cys Asn Thr Asp Ser Pro
        140                 145                 150 ctg cgc tat gtg gac att gcc atc cca tgc aac aac aag gga gct cac     592
Leu Arg Tyr Val Asp Ile Ala Ile Pro Cys Asn Asn Lys Gly Ala His
    155                 160                 165 tca gtg ggt ctg atg tgg tgg atg ctg gcc agg gaa gta ctc cgc atg     640
Ser Val Gly Leu Met Trp Trp Met Leu Ala Arg Glu Val Leu Arg Met
170                 175                 180                 185 cga ggt act atc tcc cgt gag cac ccc tgg gag gtc atg cct gat ctt     688
Arg Gly Thr Ile Ser Arg Glu His Pro Trp Glu Val Met Pro Asp Leu
```

```
                      190                 195                 200
tac ttc tac aga gac cca gag gag att gag aag gag gag cag gct gct       736
Tyr Phe Tyr Arg Asp Pro Glu Glu Ile Glu Lys Glu Glu Gln Ala Ala
            205                 210                 215 gct gag aag gct gtg acc aag gag gaa ttc cag ggt gaa tgg acc gca       784
Ala Glu Lys Ala Val Thr Lys Glu Glu Phe Gln Gly Glu Trp Thr Ala
                220                 225                 230 cca gct cct gag ttc act gct gct cag cct gag gtg gcc gac tgg tct       832
Pro Ala Pro Glu Phe Thr Ala Ala Gln Pro Glu Val Ala Asp Trp Ser
235                 240                 245 gag ggt gtg cag gtt ccc tct gtg ccc atc cag cag ttc ccc acg gaa       880
Glu Gly Val Gln Val Pro Ser Val Pro Ile Gln Gln Phe Pro Thr Glu
250                 255                 260                 265 gac tgg agt gca cag cca gcc act gag gat tgg tca gca gct ccc aca       928
Asp Trp Ser Ala Gln Pro Ala Thr Glu Asp Trp Ser Ala Ala Pro Thr
                270                 275                 280 gcg cag gcc act gag tgg gtt gga gcc acc act gag tgg tcc               970
Ala Gln Ala Thr Glu Trp Val Gly Ala Thr Thr Glu Trp Ser
            285                 290                 295 tgagctgctg tgcaggtgcc tgagcaaagg gaaaaaagat ggaaggaaaa taaagttgct    1030
aaaagctgaa aaaaaaaaaa aaaaaagggg cggccgc                            1067

<210> SEQ ID NO 2
<211> LENGTH: 295
<212> TYPE: PRT
<213> ORGANISM: Mus musculus

<400> SEQUENCE: 2

Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
                20                  25                  30

Gln Met Glu Gln Tyr Ile Tyr Lys Arg Lys Ser Asp Gly Ile Tyr Ile
            35                  40                  45

Ile Asn Leu Lys Arg Thr Trp Glu Lys Leu Leu Leu Ala Ala Arg Ala
        50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
        210                 215                 220
```

-continued

```
Glu Glu Phe Gln Gly Glu Trp Thr Ala Pro Ala Pro Glu Phe Thr Ala
225                 230                 235                 240

Ala Gln Pro Glu Val Ala Asp Trp Ser Glu Gly Val Gln Val Pro Ser
                245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
        275                 280                 285

Gly Ala Thr Thr Glu Trp Ser
    290                 295

<210> SEQ ID NO 3
<211> LENGTH: 1067
<212> TYPE: DNA
<213> ORGANISM: Mus musculus
<220> FEATURE:
<221> NAME/KEY: CDS
<222> LOCATION: (86)..(970)

<400> SEQUENCE: 3
gtcgacccac gcgtccgcta cccggggacg ggtccatacg gcgttgttct tgattcccat      60
cgtaacttaa agggaaactt acaca atg tcc gga gcc ctt gac gtc ctg cag     112
                            Met Ser Gly Ala Leu Asp Val Leu Gln
                              1               5 atg aag gag gag gat gtc ctc aaa ctc ctt gct gcg gga acc cac tta     160
Met Lys Glu Glu Asp Val Leu Lys Leu Leu Ala Ala Gly Thr His Leu
 10              15                  20                  25 ggt ggc acc aac ctt gac ttt cag atg gag cag tac atc tac aaa agg     208
Gly Gly Thr Asn Leu Asp Phe Gln Met Glu Gln Tyr Ile Tyr Lys Arg
                 30                  35                  40 aaa agt gac ggt atc tac atc ata aac ctg aag agg acc tgg gag aag     256
Lys Ser Asp Gly Ile Tyr Ile Ile Asn Leu Lys Arg Thr Trp Glu Lys
             45                  50                  55 ctg ttg ctc gca gct cga gct att gtt gcc atc gag aat cct gct gac     304
Leu Leu Leu Ala Ala Arg Ala Ile Val Ala Ile Glu Asn Pro Ala Asp
         60                  65                  70 gtc agc gtc atc tcc tcc agg aac act ggc cag cga gct gtg ctg aag     352
Val Ser Val Ile Ser Ser Arg Asn Thr Gly Gln Arg Ala Val Leu Lys
 75                  80                  85 ttt gct gct gcc aca gga gcc act ccg atc gct ggc cgc ttc aca cct     400
Phe Ala Ala Ala Thr Gly Ala Thr Pro Ile Ala Gly Arg Phe Thr Pro
             90                  95                 100                 105 ggg acc ttc act aac cag atc caa gca gcc ttc agg gag cca cgg ctt     448
Gly Thr Phe Thr Asn Gln Ile Gln Ala Ala Phe Arg Glu Pro Arg Leu
                110                 115                 120 cta gtg gtg acc gat ccc agg gct gac cat cag cca ctc aca gag gcc     496
Leu Val Val Thr Asp Pro Arg Ala Asp His Gln Pro Leu Thr Glu Ala
            125                 130                 135 tct tat gtc aac ctg ccc acc att gct ctg tgt aac aca gat tct ccc     544
Ser Tyr Val Asn Leu Pro Thr Ile Ala Leu Cys Asn Thr Asp Ser Pro
        140                 145                 150 ctg gcg tat gtg gac att gcc atc cca tgc aac aac aag gga gct cac     592
Leu Ala Tyr Val Asp Ile Ala Ile Pro Cys Asn Asn Lys Gly Ala His
    155                 160                 165 tca gtg ggt ctg atg tgg tgg atg ctg gcc agg gaa gta ctc cgc atg     640
Ser Val Gly Leu Met Trp Trp Met Leu Ala Arg Glu Val Leu Arg Met
170                 175                 180                 185 cga ggt act atc tcc cgt gag cac ccc tgg gag gtc atg cct gat ctt     688
Arg Gly Thr Ile Ser Arg Glu His Pro Trp Glu Val Met Pro Asp Leu
                190                 195                 200
```

```
tac ttc tac aga gac cca gag gag att gag aag gag gag cag gct gct     736
Tyr Phe Tyr Arg Asp Pro Glu Glu Ile Glu Lys Glu Glu Gln Ala Ala
            205                 210                 215 gct gag aag gct gtg acc aag gag gaa ttc cag ggt gaa tgg acc gca     784
Ala Glu Lys Ala Val Thr Lys Glu Glu Phe Gln Gly Glu Trp Thr Ala
        220                 225                 230 cca gct cct gag ttc act gct gct cag cct gag gtg gcc gac tgg tct     832
Pro Ala Pro Glu Phe Thr Ala Ala Gln Pro Glu Val Ala Asp Trp Ser
235                 240                 245 gag ggt gtg cag gtt ccc tct gtg ccc atc cag cag ttc ccc acg gaa     880
Glu Gly Val Gln Val Pro Ser Val Pro Ile Gln Gln Phe Pro Thr Glu
250                 255                 260                 265 gac tgg agt gca cag cca gcc act gag gat tgg tca gca gct ccc aca     928
Asp Trp Ser Ala Gln Pro Ala Thr Glu Asp Trp Ser Ala Ala Pro Thr
            270                 275                 280 gcg cag gcc act gag tgg gtt gga gcc acc act gag tgg tcc             970
Ala Gln Ala Thr Glu Trp Val Gly Ala Thr Thr Glu Trp Ser
        285                 290                 295 tgagctgctg tgcaggtgcc tgagcaaagg gaaaaaagat ggaaggaaaa taaagttgct  1030
aaaagctgaa aaaaaaaaaa aaaaaaaggg cggccgc                          1067

<210> SEQ ID NO 4
<211> LENGTH: 295
<212> TYPE: PRT
<213> ORGANISM: Mus Musculus

<400> SEQUENCE: 4

Met Ser Gly Ala Leu Asp Val Leu Gln Met Lys Glu Glu Asp Val Leu
 1               5                  10                  15

Lys Leu Leu Ala Ala Gly Thr His Leu Gly Gly Thr Asn Leu Asp Phe
            20                  25                  30

Gln Met Glu Gln Tyr Ile Tyr Lys Arg Lys Ser Asp Gly Ile Tyr Ile
        35                  40                  45

Ile Asn Leu Lys Arg Thr Trp Glu Lys Leu Leu Leu Ala Ala Arg Ala
    50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
    130                 135                 140

Ile Ala Leu Cys Asn Thr Asp Ser Pro Leu Ala Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Lys Ala Val Thr Lys
    210                 215                 220

Glu Glu Phe Gln Gly Glu Trp Thr Ala Pro Ala Pro Glu Phe Thr Ala
225                 230                 235                 240
```

Ala Gln Pro Glu Val Ala Asp Trp Ser Glu Gly Val Gln Val Pro Ser
            245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
            275                 280                 285

Gly Ala Thr Thr Glu Trp Ser
            290                 295

<210> SEQ ID NO 5
<211> LENGTH: 295
<212> TYPE: PRT
<213> ORGANISM: Homo sapiens

<400> SEQUENCE: 5

Met Ser Gly Ala Leu Asp Val Leu Gln Met Lys Glu Glu Asp Val Leu
  1               5                  10                  15

Lys Phe Leu Ala Ala Gly Thr His Leu Gly Gly Thr Asn Leu Asp Phe
             20                  25                  30

Gln Met Glu Gln Tyr Ile Tyr Lys Arg Lys Ser Asp Gly Ile Tyr Ile
         35                  40                  45

Ile Asn Leu Lys Arg Thr Trp Glu Lys Leu Leu Leu Ala Ala Arg Ala
 50                  55                  60

Ile Val Ala Ile Glu Asn Pro Ala Asp Val Ser Val Ile Ser Ser Arg
 65                  70                  75                  80

Asn Thr Gly Gln Arg Ala Val Leu Lys Phe Ala Ala Ala Thr Gly Ala
                 85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
    210                 215                 220

Glu Glu Phe Gln Gly Glu Trp Thr Ala Pro Ala Pro Glu Phe Thr Ala
225                 230                 235                 240

Thr Gln Pro Glu Val Ala Asp Trp Ser Glu Gly Val Gln Val Pro Ser
            245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
            275                 280                 285

Gly Ala Thr Thr Asp Trp Ser
            290                 295

<210> SEQ ID NO 6

-continued

```
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 6

Arg Thr Trp Glu Lys Leu Leu Leu
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 7

Asn Thr Gly Gln Arg Ala Val Leu
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 8

Gly Glu Trp Thr Ala Pro Ala Pro
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 9

Cys Asn Thr Asp Ser Pro Leu Arg
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 10

Tyr Val Asp Ile Ala Ile Pro Cys
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 11

Thr Ile Ala Leu Cys Asn Thr Asp Ser
```

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 12

Thr Asp Ser Pro Leu Arg Tyr Val Asp
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 13

Pro Leu Arg Tyr Val Asp Ile Ala Ile
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 14

Val Asp Ile Ala Ile Pro Cys Asn Asn
  1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 15

Ser Pro Leu Arg Tyr Val Asp Ile Ala Ile
  1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 16

Gly Glu Trp Thr Ala Pro Ala Pro Glu Phe
  1               5                  10

<210> SEQ ID NO 17
<211> LENGTH: 10
<212> TYPE: PRT
<213> ORGANISM: Mus musculus

<400> SEQUENCE: 17

```
Ala Gln Pro Glu Val Ala Asp Trp Ser Glu
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 18

Gln Val Pro Ser Val Pro Ile Gln Gln Phe
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 19

Ser Ala Ala Pro Thr Ala Gln Ala Thr Glu
 1               5                  10

<210> SEQ ID NO 20
<211> LENGTH: 10
<212> TYPE: PRT
<213> ORGANISM: Homo sapiens

<400> SEQUENCE: 20

Thr Glu Trp Val Gly Ala Thr Thr Asp Trp
 1               5                  10

<210> SEQ ID NO 21
<211> LENGTH: 4
<212> TYPE: PRT
<213> ORGANISM: Mus musculus

<400> SEQUENCE: 21

Lys Leu Leu Ala
 1

<210> SEQ ID NO 22
<211> LENGTH: 8
<212> TYPE: PRT
<213> ORGANISM: Mus musculus

<400> SEQUENCE: 22

Lys Leu Leu Ala Ala Thr Gly His
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 23

Tyr Ile Tyr Lys Arg Lys Ser Asp
 1               5

<210> SEQ ID NO 24
```

```
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 24

Thr Pro Ile Ala Gly Arg Phe Thr
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 25

Val Asn Leu Pro Thr Ile Ala Leu
 1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 26

Met Ser Gly Ala Leu Asp Val Leu Gln Met Lys Glu
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 27

Leu Asp Val Leu Gln Met Lys Glu Glu Asp Val Leu
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 28

Gln Met Lys Glu Glu Asp Val Leu Lys Leu Leu Ala
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 29

Lys Leu Leu Ala Ala Gly Thr His Leu Gly Gly Thr
```

```
<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 30

Gln Met Glu Gln Tyr Ile Tyr Lys Arg Lys Ser Asp
  1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 31

Tyr Ile Tyr Lys Arg Lys Ser Asp Gly Ile Tyr Ile
  1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 32

Ile Asn Leu Lys Arg Thr Trp Glu Lys Leu Leu Leu
  1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 33

Arg Thr Trp Glu Lys Leu Leu Leu Ala Ala Arg Ala
  1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 34

Ile Ser Ser Arg Asn Thr Gly Gln Arg Ala Val Leu
  1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide
```

```
<400> SEQUENCE: 35

Asn Thr Gly Gln Arg Ala Val Leu Lys Phe Ala Ala
  1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 36

Ala Thr Gly Ala Thr Pro Ile Ala Gly Arg Phe Thr
  1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 37

Thr Pro Ile Ala Gly Arg Phe Thr Pro Gly Thr Phe
  1               5                  10

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 38

Glu Ala Ser Tyr Val Asn Leu Pro Thr Ile Ala Leu Cys Asn Thr Asp
  1               5                  10                  15

Ser Pro Leu Arg Tyr Val Asp Ile Ala Ile Pro Cys Asn Asn Lys
             20                  25                  30

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 39

Glu Ala Ser Tyr Val Asn Leu Pro Thr Ile Ala Leu
  1               5                  10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 40

Val Asn Leu Pro Thr Ile Ala Leu Cys Asn Thr Asp
  1               5                  10
```

```
<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 41

Thr Ile Ala Leu Cys Asn Thr Asp Ser Pro Leu Arg
 1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 42

Cys Asn Thr Asp Ser Pro Leu Arg Tyr Val Asp Ile
 1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 43

Ser Pro Leu Arg Tyr Val Asp Ile Ala Ile Pro Cys
 1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 44

Tyr Val Asp Ile Ala Ile Pro Cys Asn Asn Lys Gly
 1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 45

Glu Glu Phe Gln Gly Glu Trp Thr Ala Pro Ala Pro
 1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 46
```

```
Gly Glu Trp Thr Ala Pro Ala Pro Glu Phe Thr Ala
1               5                   10
```

<210> SEQ ID NO 47
<211> LENGTH: 12
<212> TYPE: PRT
<213> ORGANISM: Mus musculus

<400> SEQUENCE: 47

```
Glu Phe Thr Ala Ala Gln Pro Glu Val Ala Asp Trp
1               5                   10
```

<210> SEQ ID NO 48
<211> LENGTH: 12
<212> TYPE: PRT
<213> ORGANISM: Mus musculus

<400> SEQUENCE: 48

```
Ala Gln Pro Glu Val Ala Asp Trp Ser Glu Gly Val
1               5                   10
```

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 49

```
Ser Glu Gly Val Gln Val Pro Ser Val Pro Ile Gln
1               5                   10
```

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 50

```
Gln Val Pro Ser Val Pro Ile Gln Gln Phe Pro Thr
1               5                   10
```

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 51

```
Thr Glu Asp Trp Ser Ala Ala Pro Thr Ala Gln Ala
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 52

```
Ser Ala Ala Pro Thr Ala Gln Ala Thr Glu Trp Val
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 53

Thr Ala Gln Ala Thr Glu Trp Val Gly Ala Thr Thr
 1               5                  10

<210> SEQ ID NO 54
<211> LENGTH: 11
<212> TYPE: PRT
<213> ORGANISM: Homo sapiens

<400> SEQUENCE: 54

Thr Glu Trp Val Gly Ala Thr Thr Asp Trp Ser
 1               5                  10

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 55

Leu Leu Leu Ala Ala Arg Ala Ile Val
 1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 56

Leu Ala Ala Arg Ala Ile Val Ala Ile
 1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 57

Pro Leu Arg Tyr Val Asp Ile Ala Ile Pro
 1               5                  10

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 58

Glu Ala Ser Tyr Val Asn Leu Pro Thr Ile Ala Leu Cys Asn Thr Asp

```
                1               5                  10                 15
Ser Pro Leu Arg Tyr Val Asp Ile Ala Ile Pro Cys Asn Asn Lys Gly
            20                  25                 30
```

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 59

```
Glu Ala Ser Tyr Val Asn Leu Pro Thr
  1               5
```

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 60

```
Ala Ser Tyr Val Asn Leu Pro Thr Ile
  1               5
```

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 61

```
Ser Tyr Val Asn Leu Pro Thr Ile Ala
  1               5
```

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 62

```
Tyr Val Asn Leu Pro Thr Ile Ala Leu
  1               5
```

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 63

```
Val Asn Leu Pro Thr Ile Ala Leu Cys
  1               5
```

<210> SEQ ID NO 64
<211> LENGTH: 9
<212> TYPE: PRT
<213> ORGANISM: Artificial Sequence

```
<220> FEATURE:
<223> OTHER INFORMATION: Description of Artificial Sequence:
      Illustrative mouse/human peptide

<400> SEQUENCE: 64

Asn Leu Pro Thr Ile Ala Leu Cys Asn
 1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 65

Leu Pro Thr Ile Ala Leu Cys Asn Thr
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 66

Pro Thr Ile Ala Leu Cys Asn Thr Asp
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 67

Thr Ile Ala Leu Cys Asn Thr Asp Ser
 1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 68

Ile Ala Leu Cys Asn Thr Asp Ser Pro
 1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 69

Ala Leu Cys Asn Thr Asp Ser Pro Leu
 1               5
```

```
<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 70

Leu Cys Asn Thr Asp Ser Pro Leu Arg
 1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 71

Cys Asn Thr Asp Ser Pro Leu Arg Tyr
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 72

Asn Thr Asp Ser Pro Leu Arg Tyr Val
 1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 73

Thr Asp Ser Pro Leu Arg Tyr Val Asp
 1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 74

Asp Ser Pro Leu Arg Tyr Val Asp Ile
 1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 75
```

-continued

```
Ser Pro Leu Arg Tyr Val Asp Ile Ala
  1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 76

Pro Leu Arg Tyr Val Asp Ile Ala Ile
  1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 77

Leu Arg Tyr Val Asp Ile Ala Ile Pro
  1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 78

Arg Tyr Val Asp Ile Ala Ile Pro Cys
  1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 79

Tyr Val Asp Ile Ala Ile Pro Cys Asn
  1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 80

Val Asp Ile Ala Ile Pro Cys Asn Asn
  1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence:
```

```
             Illustrative mouse/human peptide

<400> SEQUENCE: 81

Asp Ile Ala Ile Pro Cys Asn Asn Lys
  1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence:
      Illustrative mouse/human peptide

<400> SEQUENCE: 82

Ile Ala Ile Pro Cys Asn Asn Lys Gly
  1               5
```

CANCER VACCINES CONTAINING EPITOPES OF ONCOFETAL ANTIGEN

PRIORITY

This application is a continuation of U.S. application Ser. No. 10/523,277, filed Sep. 22, 2005, now U.S. Pat. No. 7,718,762 which is a national phase entry under 35 U.S.C. §371 of International Application No. PCT/US03/24518 filed Aug. 4, 2003, which claims the benefit of the filing date of U.S. Provisional Application No. 60/400,851, filed Aug. 2, 2002.

STATEMENT REGARDING GOVERNMENTAL SUPPORT

Work leading to the disclosed invention was funded in part by The National Institutes of Health grant no. RO1-CA82603-01A251. Therefore, the Government may have certain rights in the invention.

BACKGROUND OF THE INVENTION

Cancer is one of the three leading causes of death in industrialized nations. As treatment and preventative measures for infectious diseases and cardiovascular disease continue to improve, and the average life expectancy increases, cancer is likely to become the most common fatal disease. In developed countries, about one person in three receives a diagnosis of cancer during his or her lifetime and almost one in four dies from it.

Cancers are the progressive growth of the progeny of a single transformed cell. A tumor or neoplasm is a population of cells that exhibit uncontrolled proliferation without regard to normal bodily requirements. A malignant neoplasm or cancer is one that threatens life by invading and destroying adjacent tissue and/or by seeding (metastasizing) to distant sites. Malignant tumors are divided into carcinomas (which arise from epithelial precursor cells), sarcomas (which arise largely from mesenchymal tissues) and lymphomas (which arise from precursors of red and white blood cells). Therefore, curing cancer requires that all the malignant cells be removed or destroyed without killing the patient. Unfortunately, the overt manifestation and initial clinical presentation of cancer usually occur at a late stage in the disease process when the capacity for invasion has already been unleashed. By the time of diagnosis, a high proportion of patients have occult or even clinically detectable metastases. The capacity of conventional cytotoxic approaches to succeed in the face of this advanced, accelerating disease has, unfortunately, been limited (1,2). In contrast to the short time between disease presentation and established metastasis, the period of transition from hyperproliferative, but noninvasive disease (3-5) to invasive cancer may be 10 years or more in humans. For breast cancer, this period is estimated to average 6 years (3,4).

A major problem confronting cancer researchers in developing immunological weapons against this disease is simply that these cells closely resemble the normal lineages from which they arise. Thus, despite major advances in the understanding of the factors that lead to the development of cancer, progress in the clinical management of cancer remains limited. This is due in large part to the limited success of conventional therapy in the treatment of metastasis.

Early research revealed that mouse tumors displayed molecules that led to rejection of tumor cells when transplanted into syngeneic (i.e., genetically identical) animals. These molecules are "recognized" by T-cells in the recipient animal, and provoke a cytolytic T-cell response with lysis of the transplanted cells. This evidence was first obtained with tumors induced by chemical carcinogens. The antigens expressed by the tumors that elicited the T-cell response were found to be different for each tumor. This class of antigens has come to be known as "tumor specific transplantation antigens" or "TSTAs". Following the observation of the presentation of such antigens when induced by chemical carcinogens, similar results were obtained when tumors were induced via ultraviolet radiation. See Kripke, J. Natl. Canc. Inst. 53:333-336 (1974).

A class of antigens has been recognized which are presented on the surface of tumor cells and are recognized by cytolytic T cells, leading to tumor cell lysis. This class of immunogenic antigens that arouse T-cell mediated immune reactions in the cancer-bearing host is known as "tumor rejection antigens" or "TRAs". The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells expressing the tumor rejection antigens are lysed. Characterization studies have identified CTL clones that specifically lyse cells expressing the tumor rejection antigens. Examples of this work may be found in Levy, et al., Adv. Cancer Res. 24:1-59 (1977); Boon, et al., J. Exp. Med. 152:1184-1193 (1980); Brunner, et al., J. Immunol. 124:1627-1634 (1980); Maryanski, et al., Eur. J. Immunol. 124:1627-1634 (1980); Maryanski, et al., Eur. J. Immunol. 12:406-412 (1982); Palladino, et al., Canc. Res. 47:5074-5079 (1987).

The immune system responds to cancer cells in complicated ways. There are two main types of immune cells that play a significant role in combating disease: B (or bone marrow-derived) lymphocytes ("B cells) produce antibodies to foreign antigens (which constitutes the part of the immune system known as humoral immunity); and T (or thymus-derived) lymphocytes ("T cells") are involved in cell-mediated immunity. There are three main subclasses of T cells, namely, helper cells, cytotoxic cells and suppressor cells often referred to as CD4 Th cells, CD8 Tc cells and CD8 Ts cells, respectively, on account of their reactivity with a group ("cluster") of monoclonal antibodies specific to a surface marker that identifies a particular lineage or differentiation stage. Thus, all leukocyte surface antigens whose structures are defined are given a "CD" (cluster of differentiation) designation, i.e., CD4 and CD8 respectively. The presence of a TRA on a tumor cell is recognized by the T cells and antigen processing cells as a "non-self" or foreign antigen. T cells react with foreign antigens via receptors on their surfaces. The human immune system contains millions of clones of T cells, each of which has distinctive surface receptors. The physical properties of these receptors confer specific binding capabilities and permit each of the several million clones of T cells in an individual to operate independently. The T cell receptor is capable of recognizing a particular antigen only when it is associated with a surface marker on an antigen-presenting cell (APC), such as a dendritic cell or a macrophage. The surface markers belong to a group of molecules known as the major histocompatibility complex (MHC). Explained in the context of cancer, a tumor rejection antigen is acquired and processed by APC. The APC processes the antigenic protein into shorter peptides called epitopes that generally range from about 8 to about 12 amino acids in length. If the peptides are presented on class I MHC proteins to CD8 T cells, then the epitopes are usually about 8 amino acids in length. If the peptides are presented on class II MHC molecules to CD4 T cells, then the epitopes are usually 9-12 amino acids in length. Binding of the T cell receptor to the epitope of the antigen on the antigen-presenting cell induces changes in the T cell that triggers a cell-mediated immune response.

Two signals are primarily responsible for inducing the T cell mediated response to an APC associated with an epitope of an antigen. A first signal results from the binding cross-linking of the T cell receptors with the epitope:MHC protein complex. A second, co-stimulatory signal is sent by "accessory" membrane molecules on the APC when bound by their receptors on the responding T cell. Subsequent to the resulting activation of T cells is the secretion of soluble intercellular messengers, known generically as "cytokines", which regulate the amplitude or intensity and duration of the immune response. Cytokines include the group of biomolecules formerly known as lymphokines, monokines, interleukins and interferons (*Essential Immunology*, seventh edition, Blackwell Scientific Publications, Oxford, Great Britain, 1991, pp. 140-150). In this fashion, T cytotoxic cells that recognize and are specific to the tumor rejection antigen are stimulated and attack tumor cells that express the antigen.

Malignant tumors have been treated with chemotherapeutic agents that directly impair tumor cells or with immunotherapeutic agents that cause non-specific activation of immunity of a host. In recent years, researchers using tumors of animals, mainly mice, have revealed that tumors can be completely cured by enhancing an antigen-specific immune response to tumor-related antigens and/or tumor-specific antigens present in various tumor cells. The treatment has been conducted in the clinic by enhancing the antigen-specific immune response to these tumor-specific antigens. It is now known, however, that the immune response mediated by the T cells acts either protectively or in a suppressive manner depending upon whether T cytotoxic cells and T suppressor cells are activated. Thus, tumor cells can modulate anti-tumor immunity by expressing antigens that preferentially activate Ts cells or by secreting cytokines that directly suppress or induce secretion of suppressive cytokines by T-cells. That is, the activated CD8 T cells will either recognize and kill the tumor cell carrying the appropriate epitope on its MHC class I molecule, or it will recognize and become tolerant to the tumor cell, depending on the type of the stimulated CD8 cell, cytotoxic or suppressor, respectively.

Active immunization with some tumor antigens or irradiated, autologous tumor cells themselves has been shown in experimental animals to induce T lymphocyte-mediated immunity which protects the immunized mice from subsequent challenge with histocompatible tumor cells (6-8). In various preclinical studies (9), immunologic destruction of emerging tumors due to T lymphocyte recognition of tumor antigens has appeared to involve $CD8^+$ cytotoxic T (Tc) cells, but $CD4^+$ T helper 1 (Th1) cells have also been shown to be important (10). Within the last few years, a number of such antigens have been identified (8, 11) that appear to be encoded by genes with tumor-specific expression, expressed in normal cells, but which have developed point mutations in the tumor cell, 3) for differentiation antigens, or 4) which are over-expressed in certain tumors (12, 13). Many of these tumor antigenic markers will not serve as auto-immunogens when expressed in the host and, therefore, not elicit protective T lymphocyte responses (11,14). The differentiation antigens would normally not be expected to raise an immune response due to clonal deletion of auto reactive T lymphocytes. In some cases, they do because the site of normal expression of those genes is in immune-privileged tissues such as the testis or the eye (11).

The ideal tumor antigen for use in a vaccine or at which to direct immunotherapy would be one which is present on all tumor types, absent or masked in normal tissues, evolutionarily conserved, and its function required for the malignancy of the tumor cells. Such an immunogen would be less likely to be able to be down regulated or mutated and still have the tumor cells grow and metastasize optimally. Thus, if tumor cells used such mechanisms to evade the immune response to that immunogen (15), the tumor cells would be reducing their ability to thrive.

Applicants discovered that tumor cells express a common antigen which was originally called oncofetal antigen (OFA). This protein was detected in early to mid gestation fetal cells, hence the term "Oncofetal Antigen". It is comprised of a single polypeptide chain of 295 amino acids and has a molecular weight of about 37-44 kDa. OFA was identified by Applicants to be a universal tumor specific transplantation antigen as it was detected on chemical or irradiation induced rodent tumors. All tumors that Applicants have tested were shown to express OFA (1, 43, 44). The tumors include chemically- and virally-induced sarcomas, X-irradiation-induced T cell lymphomas, and many tumors of inbred rodents reported by others to express only a unique, non-shared TSTA. Besides rodent tumors, approximately 500 human tumors representing most cancer types have been tested—all were found to express OFA (43-45). For example, OFA is also expressed by carcinomas of the breast, kidney, lung, colon, gastric mucosa, larynx, pharynx, ovary and prostate whereas normal tissues of the same types do not express OFA (43-45). OFA is believed to play an important role in tumor progression and has been implicated in tumor invasiveness, metastasis and growth.

Oncofetal antigen has recently been cloned. Complementary DNA sequence alignments have revealed 99% identity with another human protein called immature laminin receptor protein (iLRP). Hence, these two proteins are believed to be identical. (Hereinafter, the terms "OFA," "iLRP," "OFA/iLRP" and "iLRP/OFA" are used interchangeably.) The mature form of this laminin receptor appears to be a dimer of acylated immature 32 kDa laminin receptor protein (iLRP) (16). Although the mature 67 kDa form is on many normal cells as well as on tumor cells, there appears to be a preferential expression of the 32 kDa iLRP by fetal and tumor cells (17, 18). The iLRP is evolutionarily conserved (19). Indeed, the amino acid sequence of the human iLRP differs from that of murine iLRP by only four amino acids (20).

Tumor invasion of host tissues and trophoblastic penetration of the endometrium share common biological features. Both processes involve the invasion of basement membrane, an event that is initiated by adhesion of cancer or trophoblast cells to basement membrane components and particularly to laminin. Adhesion to laminin is mediated through a variety of cell surface receptors. Other investigators (Van den Brule F A, et al., Biochem. Biophys. Res. Commun. 201:388-393 (1994)), have shown that the 67 kD laminin receptor (67LR) and galectin-3 are inversely modulated as the invasive phenotype of cancer cells progresses, with up regulation of the former, and down regulation of the latter, respectively. These investigators found that the 67LR expression levels in the fetus increased from the $7^{th}$ week of gestation to a maximum at the $12^{th}$ week, when invasion is maximal, and then declined. Expression of galectin-3 was inversely modulated by the gestational age, with a minimum expression at the $12^{th}$ week of gestation. A year earlier (1993), and 6 years before our identification of Oncofetal Antigen as iLRP, Applicants reported (in Coggin et al., Arch. Otolaryngol. Head Neck Surg. 119:1257-1266 (1993)) that based on the results of flow cytometry using different strains of mice, that the proportion of cells expressing OFA increased gradually during the gestational life of the fetus to reach its maximum levels (29% of the cells) at mid-gestation (day 13) and thereafter dropped gradually to 5% at day 18, whereas newborn mice did not show increased levels of expression of OFA.

The transition from in situ tumor growth to metastatic disease is defined by the ability of tumor cells of the primary site to invade local tissues and to cross tissue barriers. To initiate the metastatic process, cancer cells must adhere to extracellular matrix (ECM) components, secrete proteases which digest the dense matrix of type IV collagen, glycoproteins, and proteoglycans allowing them to invade the interstitial stroma and respond to factors inducing motility of the invasive cells (21). For distant metastases, intravasation requires tumor cell invasion of the subendothelial basement membrane of blood vessels using the same mechanisms (22). Several published experiments have suggested that tumor cell interaction with the laminin component of the ECM is important to the expression of the metastatic phenotype (23, 24). Upon binding of laminin by the immature form of the high affinity laminin receptor (iLRP), its expression and that of the laminin-binding $\alpha 6\beta 1$ or 4 integrin are enhanced (25, 26). Thus, the stability of laminin binding by the tumor cells is enhanced. Besides this, the same step induces production and secretion of the collagenase IV matrix metalloproteinases (27, 28) required for digestion of the ECM to allow metastasis to occur. Increased expression of collagenase IV is seen in invasive colonic, gastric, ovarian, and thyroid adenocarcinomas while benign proliferative disorders of the breast and colon and normal colorectal and gastric mucosa have low or no staining for these proteases (29,30). Increased expression of iLRP is also seen in a wide variety of human adenocarcinomas, including those of the colon, breast, stomach, and liver (29, 31). Over-expression of iLRP is associated with poor prognosis in several types of tumor (32-35). In breast carcinoma, over-expression of iLRP correlates with early dissemination of the tumor cells to the bone marrow that further emphasizes the role of iLRP in the metastatic process (36). Experimental administration of anti-iLRP antibody or anti-laminin antibody at the time of tumor cell injection inhibits tumor metastasis (37-39).

OFA/iLRP is immunogenic. OFA/iLRP-specific T cells cloned from irradiated mice have been identified as Th1-type CD4+ T cells, which produce interferon-gamma, or cytotoxic T cells which secrete interferon-$\gamma$. Also, CD8+ suppressor T cells, which secrete IL-10 are induced. In addition, stimulating peripheral blood mononuclear cells from patients with breast cancer with autologous tumor cells resulted in the expansion of tumor reactive T cells. Analysis of these tumor reactive T-cells cloned by Applicants revealed that a substantial proportion of the clones showed reactivity against purified OFA/iLRP.

In more recent experiments, Applicants have observed that immunization of mice with syngeneic tumor cells expressing iLRP resulted in cross-reactive protective immunity against a spectrum of syngeneic tumors because they all express iLRP (6, 7). Immunization with iLRP:nitrocellulose particles produced distinct T and B cell mediated immunity depending on the dose of iLRP used. Thus, immunization with the intact iLRP protein can induce effector or regulatory T cells depending on the dose used.

The OFA/iLRP also activates $T_s$ cells. They secrete IL-10. $T_s$ cells prevent $T_c$ cells from exhibiting cytotoxic activity against tumor cells. Once the concentration of iLRP reaches a certain optimal concentration, it induces IL-10-producing Ts cells that prevent $T_c$ cells from killing antigen-positive target tumor cells. This phenomenon caused by an excess of the T cell immunogen, 37-44 kDaOFA, enables the immune system to suppress $T_c$-mediated immunity. In other words, it is an immuno-regulatory controlled measure that prevents over-production of $T_c$ cells to any $T_c$-antigen. This immuno-regulation prevents anti-self $T_c$-mediated immunity and other anti-self immunity.

Rohrer et al. (40) showed that the apparent tumor-free, long-term survivors of fractionated, sublethal x-irradiation had developed iLRP-specific memory Th1 and Tc lymphocytes even though they showed no sign of lymphoma development. Approximately, half of the RFM mice that were irradiated died within 6 months after irradiation with metastatic thymic lymphoma (41). Besides the memory effector Th1 and Tc lymphocytes induced by iLRP during tumor development, non-cytotoxic, iLRP-specific, CD8$^+$ T cells that secreted IL-10 upon antigen stimulation were also cloned from those long-term RFM mouse radiation survivors (40, 42). The IL-10 inhibited Tc activity (42) and so these cells can dampen anti-tumor immunity of whatever specificity. We suggested that the time of appearance and/or the relative number of IL-10-secreting CD8 T lymphocytes compared to that of iLRP-specific Tc cells may have been a factor in determining whether an irradiated RFM mouse developed a thymic lymphoma and died from it subsequent to X-irradiation (43). In this regard, Applicants have observed that during breast or renal cell carcinoma development in humans, iLRP-specific Th1, Tc, and IL-10-secreting, CD8$^+$ T (Ts) lymphocytes were clonable from the patients' peripheral blood (44, 45). Consistent with their view of the contribution of the Ts cells to tumor progression (43), Applicants have also found that breast cancer patients with the highest ratio of iLRP-specific Ts:Tc lymphocytes required a second surgery due to tumor recurrence (44). Thus, the frequency of the IL-10-secreting, iLRP-specific Ts lymphocytes in cancer patients may be used as a prognostic for clinical response to therapy (44). Such methods are a subject of U.S. Pat. No. 6,335,174.

Thus, while use of OFA/iLRP for cancer therapy and as a vaccine holds promise, it is tempered by the possibility that such uses will also trigger Ts-mediated immuno-regulation. In this regard, Rohrer et al., Mod. Asp. Immunobiol. 1(5): 191-195 (2001), state that it is important to define the peptide epitopes which stimulate iLRP/OFA-specific Tc, Th and the IL-10 secreting Ts cells in order to determine if the epitopes which stimulate the Ts cells are different than and located on a different portion of the OFA protein than the epitopes that stimulate the Tc and/or Th cells.

SUMMARY OF THE INVENTION

The speculation in the Rohrer publication aside, the facts remain that OFA/iLRP-specific Tc and Ts cells are both CD8 T cells and that with the exception of the spectrum of cytokines that they produce, their functionally abilities are basically the same. Applicants had also shown that Ts cells display Tc-like cytotoxic activity in the presence of anti-IL-10 antibodies (which neutralize the IL-10 secreted by the Ts cells). Further, the Rohrer publication also demonstrated that the relative stimulation of Tc and Ts cells by OFA/iLRP in mice was dose-dependent; since Ts cells have lower affinity T cell antigen receptors (TCRs) compared to TCRs on Tc cells, Tc cells responded to significantly smaller doses of OFA/iLRP than Ts cells. These findings suggested that dosage amount (as opposed to the epitope itself) is an important variable in potentiating an immune response without stimulating Ts cells. On the basis of these facts and observations, persons skilled in the art would have expected Tc and Ts cells to be reactive to the same spectrum of OFA epitopes.

Applicants have now discovered distinct, non-overlapping OFA fragments containing epitopes that stimulate one class or subclass of T cells versus other classes. One aspect of the present invention is directed to OFA epitopes that specifically stimulate Tc cells. Another aspect of the present invention is directed to OFA epitopes that specifically stimulate Ts cells. Yet another aspect of the present invention is directed to OFA epitopes that specifically stimulate Th cells. DNAs encoding the OFA fragments and epitopes, and methods of making the epitopes are also provided.

Another aspect of the present invention is directed to a method for identifying epitopes of mammalian OFA that stimulate T cytotoxic cells or T suppressor cells relative to other T cells, in mammals. The method entails a) obtaining a sample of peripheral blood leukocytes (PBLs) or splenocytes from a tumor-bearing mammal; b) clonally expanding T cells of different T cell subclasses present in the sample and that are specific to OFA, thus producing clones of T cells of different T cell subclasses; c) determining subclass type of each of the clones of T cell subclasses; d) culturing the clones of T cells of (c) in the presence of a deletion mutant of OFA; and e) comparing extent of stimulation of clones of T cells of one subclass by the OFA deletion mutant to stimulation of clones of T cells of other T cell subclasses by the OFA deletion mutant; wherein greater stimulation of a clone of T cells of one subclass relative to that of other T cell subclasses by the OFA deletion mutant is indicative that the OFA deletion mutant contains an epitope that stimulates T cells of one subclass relative to the other T cell subclasses.

In some embodiments, the sample contains splenocytes obtained from a mouse. In other embodiments, the mammal is a human and the sample comprises PBLs. In some embodiments, (e) comprises comparing stimulation of the clones of T cells of the subclass by the OFA epitope to two controls, wherein the first control comprises intact OFA and the second control comprises an OFA mutant that lacks the epitope. In yet other embodiments, (d) and (e) are repeated using a plurality of OFA deletion mutants wherein each OFA deletion mutant lacks a different portion of the entire OFA molecule.

OFA epitopes disclosed herein are therapeutically useful in mammals. Accordingly, a further aspect of the present invention is directed to compositions containing at least one OFA epitope that stimulates or induces T cytotoxic cells. In preferred embodiments, this aspect of the present invention is directed to an immunotherapeutic composition e.g., a vaccine, comprising or consisting essentially of a plurality of OFA epitopes that specifically stimulate T cytotoxic cells, and a carrier (and in preferred embodiments, a carrier which also functions as an immunopotentiating adjuvant). By the phrase "consisting essentially of" it is meant to exclude elements that would affect the basic and novel characteristics of the composition such as its immunogenic effect in terms of stimulating T cytotoxic cells relative to T suppressor cells. Thus, elements that would be excluded from the compositions include OFA epitopes (or regions of the OFA protein that contain such epitopes) that specifically stimulate T suppressor cells because their presence would cause a diminution of the therapeutic effect of the composition. The compositions may also include one or more OFA epitopes that specifically stimulate Th cells. The compositions stimulate proliferation of OFA-specific Tc cells, thus potentiating T cell-mediated immunity in mammalian cancer patients, which may inhibit growth or proliferation of cancer cells and/or induce immunity.

A further aspect of the present invention is directed to methods of making a vaccine or immunotherapeutic composition. The method entails (a) identifying a plurality of oncofetal antigen (OFA) epitopes that specifically stimulate T cytotoxic lymphocytes in the mammal (e.g., human); and (b) formulating two or more of the epitopes identified in (a) with a carrier, thus forming the immunotherapeutic composition. In other embodiments, the method further entails c) identifying a plurality of oncofetal antigen (OFA) epitopes that specifically stimulate T helper lymphocytes in the mammal (e.g., human), and wherein b) comprises formulating one or more of the OFA epitopes identified in c) with the two or more epitopes identified in a), along with the carrier.

The OFA epitopes of the present invention that specifically stimulate Tc cells and optionally, the OFA epitopes that specifically stimulate Th cells may be administered to cancer patients, preferably in together in the form of a composition. Thus, the present invention further provides a method of treating cancer in a mammal, by administering to a cancer patient at least one and preferably a plurality of oncofetal antigen (OFA) epitopes that specifically stimulate T cytotoxic lymphocytes in the mammal, and optionally, one and preferably a plurality of oncofetal antigen (OFA) epitopes that specifically stimulate T helper lymphocytes in the mammal. A related aspect of the invention is directed to a method of potentiating a T cell-mediated immune response in a mammalian cancer patient comprising administering to the cancer patient an immunogenic amount of a composition as described herein.

The OFA epitopes of the present invention provide a refined, customized approach for selectively stimulating the immune system to enhance cytotoxic anti-tumor cell activity. Embodiments of the present invention serve to reduce immuno-regulation associated with the stimulation of T suppressor cells caused by intact OFA/iLRP, thus allowing T cytotoxic cells to continue mounting an attack against tumor cells, especially when tumor burden increases.

DETAILED DESCRIPTION OF THE INVENTION

Below is an alignment of the full-length cDNA sequence of 37 kDa OFA from MCA-1315 murine fibrosarcoma with the nucleotide sequence of the murine iLRP (reported in Rao, et al., Biochemistry 28:7476-7480 (1989)). The predicted amino acid is indicated under the nucleotide sequence. The stop codon is indicated by an asterisk. Nucleotide sequences in lower case print preceding the 5' end and following the 3' end are for Sal1 and Not1 sites respectively, that were used in cloning. The amino acid sequences of the two peptides (a.a. residues 18-40 and 43-52) that were derived from mAb115-affinity purified OFA are underlined. The sequence alignment revealed 99.5% identity between the nucleotide sequence of OFA and published nucleotide sequence for murine iLRP. The predicted amino acid sequence of OFA and the amino acid sequence encoded by mouse iLRP gene were 99.3% identical. The only differences were amino acid residues 18 and 155 which were phenylalanine and arginine for OFA instead of leucine and alanine in the published amino acid sequence of murine iLRP, respectively, but which were identical to those of the human iLRP sequence. (SEQ ID NOS 1 & 3 are the DNA sequences and SEQ ID NOS 2 & 4 are the encoded proteins, respectively)

```
        gtcgacCCACGCGTCCGCTACCCGG
        -85
        GGACGGGTCCATACGGCGTTGTTCTTGATTCCCATCGTAACTTAAAGGGAAACTTACACA
        -60
OFA     ATGTCCGAGCCCTTGACGTCCTGCAGATGAAGGAGGAGGATGTCCTCAAATTCCTTGCT
        60
        ||||||||||||||||||||||||||||||||||||||||||||||||||| |||||||
iLRP    ATGTCCGAGCCCTTGACGTCCTGCAGATGAAGGAGGAGGATGTCCTCAAACTCCTTGCT
         M   S   G   A   L   D   V   L   Q   M   K   E   E   D   V   L   K   F/L L   A
         a.a.'s 1-20

OFA     GCGGGAACCCACTTAGGTGGCACCAACCTTGACTTTCAGATGGAGCAGTACATCTACAAA
        120
        ||||||||||||||||||||||||||||||||||||||||||||||||||||||||||||
iLRP    GCGGGAACCCACTTAGGTGGCACCAACCTTGACTTTCAGATGGAGCAGTACATCTACAAA
         A   G   T   H   L   G   G   T   N   L   D   F   Q   M   E   Q   Y   I   Y   K
         a.a.'s 21-40

OFA     AGGAAAAGTGACGGTATCTACATCATAAACCTGAAGAGGACCTGGGAGAAGCTGTTGCTC
        180
        ||||||||||||||||||||||||||||||||||||||||||||||||||||||||||||
iLRP    AGGAAAAGTGACGGTATCTACATCATAAACCTGAAGAGGACCTGGGAGAAGCTGTTGCTC
         R   K   S   D   G   I   Y   I   I   N   L   K   R   T   W   E   K   L   L   L
         a.a.'s 41-60

OFA     GCAGCTCGAGCTATTGTTGCCATCGAGAATCCTGCTGACGTCAGCGTCATCTCCTCCAGG
        240
        ||||||||||||||||||||||||||||||||||||||||||||||||||||||||||||
iLRP    GCAGCTCGAGCTATTGTTGCCATCGAGAATCCTGCTGACGTCAGCGTCATCTCCTCCAGG
         A   A   R   A   I   V   A   I   E   N   P   A   D   V   S   V   I   S   S   R
         a.a.'s 61-80

OFA     AACACTGGCCAGCGAGCTGTGCTGAAGTTTGCTGCTGCCACAGGAGCCACTCCGATCGCT
        300
        ||||||||||||||||||||||||||||||||||||||||||||||||||||||||||||
iLRP    AACACTGGCCAGCGAGCTGTGCTGAAGTTTGCTGCTGCCACAGGAGCCACTCCGATCGCT
         N   T   G   Q   R   A   V   L   K   F   A   A   A   T   G   A   T   P   I   A
         a.a.'s 81-100

OFA     GGCCGCTTCACACCTGGGACCTTCACTAACCAGATCCAAGCAGCCTTCAGGGAGCCACGG
        360
        ||||||||||||||||||||||||||||||||||||||||||||||||||||||||||||
iLRP    GGCCGCTTCACACCTGGGACCTTCACTAACCAGATCCAAGCAGCCTTCAGGGAGCCACGG
         G   R   F   T   P   G   T   F   T   N   Q   I   Q   A   A   F   R   E   P   R
         a.a.'s 101-120

OFA     CTTCTAGTGGTGACCGATCCCAGGGCTGACCATCAGCCACTCACAGAGGCCTCTTATGTC
        420
        ||||||||||||||||||||||||||||||||||||||||||||||||||||||||||||
iLRP    CTTCTAGTGGTGACCGATCCCAGGGCTGACCATCAGCCACTCACAGAGGCCTCTTATGTC
         L   L   V   V   T   D   P   R   A   D   H   Q   P   L   T   E   A   S   Y   V
         a.a.'s 121-140

OFA     AACCTGCCCACCATTGCTCTGTGTAACACAGATTCTCCCCTGCGCTATGTGGACATTGCC
        480
        |||||||||||||||||||||||||||||||||||||||| |||||||||||||||||||
iLRP    AACCTGCCCACCATTGCTCTGTGTAACACAGATTCTCCCCTGGCGTATGTGGACATTGCC
         N   L   P   T   I   A   L   C   N   T   D   S   P   LR/A Y   V   D   I   A
         a.a.'s 141-160

OFA     ATCCCATGCAACAACAAGGGAGCTCACTCAGTGGGTCTGATGTGGTGGATGCTGGCCAGG
        540
        ||||||||||||||||||||||||||||||||||||||||||||||||||||||||||||
iLRP    ATCCCATGCAACAACAAGGGAGCTCACTCAGTGGGTCTGATGTGGTGGATGCTGGCCAGG
         I   P   C   N   N   K   G   A   H   S   V   G   L   M   W   W   M   L   A   R
         a.a.'s 161-180

OFA     GAAGTACTCCGCATGCGAGGTACTATCTCCCGTGAGCACCCCTGGGAGGTCATGCCTGAT
        600
        ||||||||||||||||||||||||||||||||||||||||||||||||||||||||||||
iLRP    GAAGTACTCCGCATGCGAGGTACTATCTCCCGTGAGCACCCCTGGGAGGTCATGCCTGAT
         E   V   L   R   M   R   G   T   I   S   R   E   H   P   W   E   V   M   P   D
         a.a.'s 181-200

OFA     CTTTACTTCTACAGAGACCCAGAGGAGATTGAGAAGGAGGAGCAGGCTGCTGCTGAGAAG
        660
        ||||||||||||||||||||||||||||||||||||||||||||||||||||||||||||
iLRP    CTTTACTTCTACAGAGACCCAGAGGAGATTGAGAAGGAGGAGCAGGCTGCTGCTGAGAAG
         L   Y   F   Y   R   D   P   E   E   I   E   K   E   E   Q   A   A   A   E   K
         a.a.'s 201-220

OFA     GCTGTGACCAAGGAGGAATTCCAGGGTGAATGGACCGCACCAGCTCCTGAGTTCACTGCT
        720
        ||||||||||||||||||||||||||||||||||||||||||||||||||||||||||||
iLRP    GCTGTGACCAAGGAGGAATTCCAGGGTGAATGGACCGCACCAGCTCCTGAGTTCACTGCT
         A   V   T   K   E   E   F   Q   G   E   W   T   A   P   A   P   E   F   T   A
         a.a.'s 221-240

OFA     GCTCAGCCTGAGGTGGCCGACTGGTCTGAGGGTGTGCAGGTTCCCTCTGTGCCCATCCAG
        780
        ||||||||||||||||||||||||||||||||||||||||||||||||||||||||||||
iLRP    GCTCAGCCTGAGGTGGCCGACTGGTCTGAGGGTGTGCAGGTTCCCTCTGTGCCCATCCAG
         A   Q   P   E   V   A   D   W   S   E   G   V   Q   V   P   S   V   P   I   Q
         a.a.'s 241-260
```

```
                                      -continued
OFA    CAGTTCCCCACGGAAGACTGGAGTGCACAGCCAGCCACTGAGGATTGGTCAGCAGCTCCC
       840
       ||||||||||||||||||||||||||||||||||||||||||||||||||||||||||||
iLRP   CAGTTCCCCACGGAAGACTGGAGTGCACAGCCAGCCACTGAGGATTGGTCAGCAGCTCCC
         Q  F  P  T  E  D  W  S  A  Q  P  A  T  E  D  W  S  A  A  P
         a.a.'s 261-280

OFA    ACAGCGCAGGCCACTGAGTGGGTTGGAGCCACCACTGAGTGGTCCTGA           888
       ||||||||||||||||||||||||||||||||||||||||||||||||
iLRP   ACAGCGCAGGCCACTGAGTGGGTTGGAGCCACCACTGAGTGGTCCTGA
         T  A  Q  A  T  E  W  V  G  A  T  T  E  W  S  *
         a.a.'s 281-295

GCTGCTGTGCAGGTGCCTGAGCAAAGGGAAAAAAGATGGAAGGAAAATAAAGTTGCTAAA
       948
                    AGCTGAAAAAAAAAAAAAAAAAAAAAGGgcggccgc
                                                      982
```

As shown below, the murine OFA and murine iLRP share 99.3% sequence similarity; there are only two differences in amino acids in the entire 295 amino acid sequence. Likewise, mouse OFA and human iLRP differ in 2 amino acids in their sequences. See, Rao, et al., Biochemistry 28:7476-7486 (1989) (murine iLRP); Yow, et al., PNAS 85:6394-6398 (1988) (human iLRP); and Coggin, et al., Anticancer Res. 19:5535-5542 (1999) (murine OFA). (SEQ ID NOS 4, 5 & 2, respectively, in order of appearance)

```
Mu iLRP    M S G A L D V L Q M K E E D V L K L L A    20
Hu iLRP    - - - - - - - - - - - - - - - - F - -
Mu OFA     - - - - - - - - - - - - - - - - F - -

A G T H L G G T N L D F Q M E Q Y I Y K    40
Hu iLRP    - - - - - - - - - - - - - - - - - - - -
Mu OFA     - - - - - - - - - - - - - - - - - - - -

R K S D G I Y I I N L K R T W E K L L L    60
Hu iLRP    - - - - - - - - - - - - - - - - - - - -
Mu OFA     - - - - - - - - - - - - - - - - - - - -

A A R A I V A I E N P A D V S V I S S R    80
Hu iLRP    - - - - - - - - - - - - - - - - - - - -
Mu OFA     - - - - - - - - - - - - - - - - - - - -

Mu iLRP    N T G Q R A V L K F A A A T G A T P I A    100
Hu iLRP    - - - - - - - - - - - - - - - - - - - -
Mu OFA     - - - - - - - - - - - - - - - - - - - -

Mu iLRP    G R F T P G T F T N Q I Q A A F R E P R    120
Hu iLRP    - - - - - - - - - - - - - - - - - - - -
Mu OFA     - - - - - - - - - - - - - - - - - - - -

Mu iLRP    L L V V T D P R A D H Q P L T E A S Y V    140
Hu iLRP    - - - - - - - - - - - - - - - - - - - -
Mu OFA     - - - - - - - - - - - - - - - - - - - -

Mu iLRP    N L P T T A L C N T D S P L A Y V D I A    160
Hu iLRP    - - - - - - - - - - - - R - - - - -
Mu OFA     - - - - - - - - - - - - R - - - - -

Mu iLRP    I P C N N K G A H S V G L M W W M L A R    180
Hu iLRP    - - - - - - - - - - - - - - - - - - - -
Mu OFA     - - - - - - - - - - - - - - - - - - - -

Mu iLRP    E V L R M R G T I S R E H P W E V M P D    200
Hu iLRP    - - - - - - - - - - - - - - - - - - - -
Mu OFA     - - - - - - - - - - - - - - - - - - - -

Mu iLRP    L Y F Y R D P E E I E K E E Q A A A E K    220
Hu iLRP    - - - - - - - - - - - - - - - - - - - -
Mu OFA     - - - - - - - - - - - - - - - - - - - -

Mu iLRP    A V T K E E F Q G E W T A P A P E F T A    240
Hu iLRP    - - - - - - - - - - - - - - - - - - - -
Mu OFA     - - - - - - - - - - - - - - - - - - - -

Mu iLRP    A Q P E V A D W S E G V Q V P S V P I Q    260
Hu iLRP    T - - - - - - - - - - - - - - - - - - -
Mu OFA     A - - - - - - - - - - - - - - - - - - -

Mu iLRP    Q F P T E D W S A Q P A T E D W S A A P    280
Hu iLRP    - - - - - - - - - - - - - - - - - - - -
Mu OFA     - - - - - - - - - - - - - - - - - - - -

Mu iLRP    T A Q A T E W V G A T T E W S              295
Hu iLRP    - - - - - - - - - - - - D - -
Mu OFA     - - - - - - - - - - - - E - -
```

Amino Acid Abbreviations:

| Alanine | A |
| Arginine | R |
| Asparagine | M |
| Aspartic Acid | D |
| Cysteine | C |
| Glutamine | Q |
| Glutamic Acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

Thus, for purposes of the present invention, murine OFA, murine iLRP, human OFA and human iLRP are collectively referred to as "OFA", and as indicated above, "OFA" and "iLRP" are used interchangeably along with "OFA/iLRP" and "iLRP/OFA". By "OFA," it is intended to mean a consensus 295 amino acid polypeptide with variability in positions 18, 155, 241 and 293 as shown. Any epitope containing an amino residue that is not common to all the aforementioned OFA and iLRP proteins as shown above, or any other mammalian OFA or iLRP, may be considered to contain at the least, variability in that position.

One aspect of the present invention is directed to epitopes of OFA that stimulate proliferation of T cells belonging to one subclass relative to one or more other subclasses; that is, they specifically stimulate Tc, Th or Ts cells. Relative or specific stimulation may be compared to a control such as IMDM (Iscove's Modified Dulbecco's Medium). Stated somewhat differently, the stimulation of a given subclass of T cells by the OFA epitope will be comparable to if not greater than the amount of stimulation of the given subclass of T cells by intact OFA. Relative stimulation of subclasses of murine T cells is quantified in the examples below. As shown in various tables in the examples below, OFA epitopes that stimulate Tc cells show as much as a 56-fold increase in stimulation of Tc cells versus Ts cells. OFA epitopes that stimulate Ts cells show as much as a 13-14-fold increase in stimulation of Ts cells versus Tc cells. Thus, unlike intact OFA, the stimulation of the other T cell subclasses induced by the epitope is comparable to a baseline or control (e.g., 2-10-fold difference with a control such as IMDM, as shown in Table 4 below). Thus, in general, by the phrase "an OFA epitope that specifically stimulates one T cell subclass (Tc, Ts or Th)," it is meant that the stimulation of that given subclass of T cells is at least about 5, 10, 15, 20, 25, 30, 35, 40, 45, 50, 55, 60-fold, or more, compared to at least one of the other T cell subclasses, particularly as between Tc and Ts cells, and Ts and Th cells.

The OFA epitopes of the present invention typically have a length of from 8-12 amino acids, although slightly shorter or longer peptides may be used, provided that they also exhibit substantially the same properties in terms of stimulation of T cells. Thus, the epitopes may also be described in terms of a peptide of from about 8 or 8 to about 12 or 12 amino acids. In the case of Th cells, epitopes can be longer e.g., up to about 20 or about 25 amino acids in length, due to differences between class I and class II MHC protein binding and presenting antigenic peptides.

OFA epitopes that specifically stimulate proliferation of clones of Tc cells (relative to Ts and Th) cells at least in mice have been found in the N-terminal and C-terminal regions of OFA. Tc epitopes containing amino acid residues 53-60 (e.g., RTWEKLLL) (SEQ ID NO: 6) or residues 81-88 (e.g., NTGQRAVL) (SEQ ID NO: 7), have been identified in the N-terminal region, and Tc epitopes containing residues 229-236 (GEWTAPAP) (SEQ ID NO: 8) have been identified in the C-terminal region. Thus, other Tc epitopes embraced by the present invention include OFA (49-60), OFA (50-61), OFA (51-62), OFA (52-63), OFA (53-64), OFA (50-60), OFA (51-61), OFA (52-62), OFA (53-63), OFA (51-60), OFA (52-61), OFA (53-62), OFA (52-60), OFA (53-61), OFA (77-88), OFA (78-89), OFA (79-90), OFA (80-91), OFA (81-92), OFA (78-88), OFA (79-89), OFA (80-90), OFA (81-91), OFA (79-88), OFA (80-89), OFA (81-90), OFA (80-88), OFA (81-89), OFA (225-236), OFA (226-237), OFA (227-238), OFA (228-239), OFA (229-240), OFA (226-236), OFA (227-237), OFA (228-238), OFA (229-239), OFA (227-236), OFA (228-237), OFA (229-238), OFA (228-236) and OFA (229-237).

Other preferred epitopes include sequences of about 8-12 amino acids and which contain CNTDSPLR (SEQ ID NO: 9) (e.g., amino acid residues 148-155) or the sequence YVDIAIPC (SEQ ID NO: 10) (e.g., amino acid residues 156-163). Thus, aside from these two sequences, additional Tc epitopes include OFA (144-155), OFA (145-156), OFA (146-157), OFA (147-158), OFA (148-159), OFA (145-155), OFA (146-156), OFA (147-157), OFA (148-158), OFA (146-155), OFA (147-156), OFA (148-157), OFA (147-155), OFA (148-156), OFA (152-163), OFA (153-164), OFA (154-165), OFA (155-166), OFA (156-167), OFA (153-163), OFA (154-164), OFA (155-165), OFA (156-166), OFA (154-163), OFA (155-164), OFA (156-165), OFA (155-163), and OFA (156-164). As per the alignment shown above, any epitopes that correspond to a fragment of OFA containing residue 155 could contain an "A" residue in its place. Other preferred epitopes include the sequence TIALCNTDS (SEQ ID NO: 11)(e.g., amino acid residues 144-152), TDSPLRYVD (SEQ ID NO: 12) (e.g., amino acid residues 150-158), PLRYVDIAI (SEQ ID NO: 13)(e.g., amino acid residues 153-161, and VDIAIPCNN (SEQ ID NO: 14)(e.g., amino acid residues 157-165). There may be in certain few instances, epitopes that are recognized by both Ts and Tc cells. However, due to the lower affinity of antigen receptors on Ts cells, when OFA/iLRP is present in limited amounts, the Tc cells will be preferentially stimulated or induced. The antigen receptors on Tc cells have relatively higher affinity for OFA/iLRP peptide:MHC protein complex, in order to give an activation signal to the Tc cell.

OFA epitopes that specifically stimulate Th cells relative to Tc and Ts cells at least in mice have been identified to include the sequence SPLRYVDIAI (SEQ ID NO: 15)(e.g., amino acid residues 152-161 of OFA). Additional OFA epitopes that specifically stimulate Th cells relative to Tc and Ts cells at least in mice have been found in the C-terminal region of OFA. Preferred epitopes in this region contain the sequences OFA (229-238) (e.g., GEWTAPAPEF) (SEQ ID NO: 16), OFA (241-250) (e.g., AQPEVADWSE) (SEQ ID NO: 17), OFA (253-262) (e.g., QVPSVPIQQF) (SEQ ID NO: 18), OFA (277-286) (e.g., SAAPTAQATE) (SEQ ID NO: 19) and OFA (285-294)(e.g., TEWVGATTDW) (SEQ ID NO: 20). Thus, OFA epitopes that specifically stimulate Th cells may contain one of these sequences, and but may also contain additional amino acids on either or both termini, to reach lengths of about 20 to about 25 amino acids. On the other hand, they may contain about 8 or 9 of the 10 amino acids (e.g., OFA (152-159, OFA (153-160), OFA (154-161), OFA (152-160), OFA 153-161), OFA (229-236), OFA (230-237), OFA (231-238), OFA (229-237), OFA (230-238), OFA (241-248), OFA (242-249), OFA (243-250), OFA (241-249), OFA (242-250), OFA (253-260), OFA (254-261), OFA (255-262), OFA (253-261), OFA (254-262), OFA (277-284), OFA (278-285), OFA (279-286), OFA (277-285), OFA (278-286), OFA (285-292), OFA (286-293), OFA (287-294), OFA (285-293 and OFA (286-294).

OFA epitopes that specifically stimulate proliferation of Ts cells (relative to Tc and Th cells) at least in mice have been found in the region containing amino acid residues 9-28 and which contain the tetrapeptide KLLA (SEQ ID NO: 21)(e.g., amino acid residues 17-20), and preferably the octapeptide KLLAATGH (SEQ ID NO: 22)(e.g., amino acid residues 17-24). Thus, representative OFA epitopes include OFA (9-20), OFA (10-20), OFA (11-20), OFA (12-20), OFA (13-20), OFA (10-21), OFA (11-21), OFA (12-21), OFA (13-21), OFA (14-21), OFA (11-22), OFA (12-22), OFA (13-22), OFA (14-22), OFA (15-22), OFA (12-23), OFA (13-23), OFA (14-23), OFA (15-23), OFA (16-23), OFA (13-24), OFA (14-24), OFA (15-24), OFA (16-24), OFA (17-24), OFA (14-25), OFA (14-25), OFA (15-25), OFA (16-25), OFA (17-25), OFA (15-26), OFA (16-26), OFA (17-26), OFA (16-27), OFA (17-27) and OFA (17-28).

Additional OFA epitopes that specifically stimulate proliferation of clones of Ts cells (relative to Tc and Th cells) at least in mice contain amino acid residues 37-44 (e.g., IYKRKSD) (SEQ ID NO: 23) and residues 97-104 of OFA (e.g., TPIAGRFT) (SEQ ID NO: 24). Thus, aside from these two sequences, additional Ts epitopes include OFA (33-44), OFA (34-45), OFA (35-46), OFA (36-47), OFA (37-48), OFA (34-44), OFA (35-45), OFA (36-46), OFA (37-47), OFA (35-44), OFA (36-45), OFA (37-46), OFA (36-44), OFA (37-45), OFA (93-104), OFA (94-105), OFA (95-106), OFA (96-107), OFA (97-108), OFA (94-104), OFA (95-105), OFA (96-106), OFA (97-107), OFA (95-104), OFA (96-105), OFA (97-105), OFA (96-104) and OFA (97-105).

Yet other OFA epitopes that stimulate proliferation of clones of Ts cells (relative to Tc and Th cells) at least in mice contains the sequence VNLPTIAL (SEQ ID NO: 25)(e.g., OFA (140-147). Thus, aside from OFA (140-147), a further list of representative OFA epitopes that stimulate Ts cells includes OFA (136-147), OFA (137-148), OFA (138-149), OFA (139-150), OFA (140-151), OFA (137-147), OFA (138-148), OFA (139-149), OFA (140-150), OFA (138-147), OFA (139-148), OFA (138-146, OFA (138-147), OFA (138-148), OFA (138-149), OFA (140-149), OFA (139-147) and OFA (140-148).

The above-referenced publication by Rohrer et al., in *Modern Aspects of* Immunobiology further states that the task of identifying OFA epitopes that potentiate anti-OFA/iLRP antitumor mediated immunity will probably not be that simple, especially when the human outbred MHC is taken into consideration. Despite this consideration, as well as the differences between the major histocompatibility class antigens in humans and their H2 counterparts in mice, Applicants have now come to believe that OFA epitopes disclosed herein are also functional in humans. See the example below entitled "Conformation of OFA Epitope binding to H-$2^d$ Class I Proteins." Regardless, OFA epitopes functional in a given mammal such as a human may be identified or confirmed in accordance with the method described below. To identify (or as the case may be, to confirm the identity of) epitopes of OFA that selectively stimulate proliferation of one subset of T cells versus one or more other subsets of T cells in a given mammal such as a human, a sample of peripheral blood mononuclear leukocytes (PBMLs) (or mononuclear leukocytes (MNLs) derived from spleen or lymph nodes) are obtained from a tumor-bearing mammal. Since OFA has been found to be a universal tumor rejection antigen in all the malignant systems tested to date, the method may be practiced with PBMLs or MNLs from any tumor-bearing mammal, including humans. The sample is then cultured in a medium containing a predetermined concentration of OFA and one or more growth factors required for growth of T cells (e.g., IL-2 and IL-6) and antigen processing cells (APCs), so as to allow expansion of the T cells present in the sample. APCs are typically present in a PBML or MNL sample. Thus, when initially establishing the tumor-reactive lymphocytes in culture, no additional APCs need to be added. However, in order to be able to restimulate and clone those reactive T lymphocytes subsequently, additional irradiated autologous (human) or syngeneic (mouse) APCs are added along with the OFA epitope or deletion mutant used for stimulation. As a result of this procedure, clones of T cells that recognize OFA may be identified. They are then counted, followed by dilution and plating out. Preferably, the limited dilution analysis entails plating the T cells out into wells to achieve a Poisson-Type distribution (e.g., wherein after terminal dilution, greater than about 37% of the wells "plated" with test lymphocytes will have no reactive T lymphocytes and dilutions are made such that there is a 90% probability that any T lymphocyte colonies that form each came from only one cell and, thus may be properly considered as clones. Following the plating out e.g., into plastic microwells, APCs, OFA and growth factors are added to each well. This procedure results in the production of clones of T cells that are specific to OFA.

Following the cloning procedure, the T cell clones are identified according to subclass type. This procedure may be accomplished in accordance with standard techniques. For example, helper T cells may be distinguished from both T suppressor and T cytotoxic cells by determining their reactivity with anti-CD4 and anti-CD8 antibodies. Th cells react with anti-CD4 antibodies and $T_s$ and $T_c$ both react with anti-CD8 antibodies. Reactivity with such antibodies may be determined in accordance with standard techniques such as flow cytometry. To distinguish $T_s$ verses $T_c$ cells, the culture medium is analyzed to detect presence of IL-10. This interleukin is produced by $T_s$ but not $T_c$ cells. Although the $T_c$ cells may be identified by default, a positive determination can also be made by analyzing the culture medium for the presence of the cytokine IFN-gamma which these cells (Tc) make (but which $T_s$ cells do not make) and an in vitro cytotoxicity test (i.e., demonstrating that these cells kill tumor cells) may also be conducted to confirm the presence of $T_c$.

Once the subsets of T cells specific to OFA have been cloned and identified, they are cultured once again with the same aforementioned ingredients except that on this occasion, a truncated OFA protein produced by an OFA deletion mutant is added to the medium. By "OFA deletion mutant" it is meant any segment of the 295 amino acid sequence of OFA. For example, the deletion mutant may constitute a fragment of OFA (e.g., amino acids 1-25 or 250-295) or the intact 295 amino acids OFA less a deletion of internal amino acids (e.g., OFA mutant containing amino acid residues 1-135 and 156-295). The relative stimulation of Th, Ts or Tc cells by the OFA deletion mutant protein may be determined using standard procedures as well. The extent of stimulation of the clones may be determined, for example, by measuring uptake by the cells of a detectably labeled nucleotide in the culture medium, such as $^3$H-thymidine or by ELISA detection of 5-bromodeoxyuridine (BudR) incorporation. In addition, the determination may be made using positive or negative tests. A "positive-type" test simply entails a comparison of the relative stimulation of the T cell clones to a single OFA deletion mutant protein added to the culture. In preferred embodiments, the test is done in a negative "manner", which uses a plurality of overlapping OFA deletion mutants, wherein the deletions taken collectively correspond to the entire OFA protein. In either case, it is preferred to compare the determined value for any given T cell clone against a control such as intact OFA per se. If the method is initially carried out with OFA deletion mutant proteins greater than about 12 amino acids in length, the stimulation of the T cell clones in subsequent determination of relative stimulation should be conducted at least one additional time, each time using a shorter OFA deletion mutant in order to identify an OFA epitope that produces maximum relative stimulation of T cells of a given subclass relative to the others.

This method may also be used to test analogs of the epitopes, e.g., that differ from the naturally occurring sequence in terms of one or more naturally or non-naturally occurring amino acid substitutions or additions, or one or more amino acid deletions. As stated above, this method may be used to determine whether epitopes corresponding to sequences containing amino acid positions 18, 155, 241 and/or 293 may contain the amino acid residue native to human or murine iLRP.

Modifications and changes may be made in the structure of the OFA epitope provided that the modification or change does not alter the epitope to the point where it does not selectively stimulate the given subclass of T cells. Such are termed "biologically functional equivalents," "functional equivalents" or "analogs," are also encompassed within the meaning of the term "OFA epitope".

For example, one of skill in the art will recognize that certain amino acids may be substituted for other amino acids in a given OFA epitope. It is also well understood by the skilled artisan that there is a limit to the number of changes that may be made within a portion of the molecule and still result in a molecule with an acceptable level of equivalent biological activity. In determining whether a given substitution, addition or deletion will result in a significant change in the desired activity, there are several general guidelines to consider. In particular, where shorter length epitopes are concerned, it is contemplated that fewer amino acids should be made within the given peptide. Longer epitopes may have an intermediate number of changes. The longest epitopes will have the most tolerance for a larger number of changes. It is also well understood that where certain residues are shown to be particularly important to the biological or structural properties of a polyamino acid, such residues may not generally be exchanged. Amino acid substitutions are generally based on the relative similarity of the 5 amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape.

Therefore, based upon these considerations, members of the following groups, namely: arginine, lysine and histidine; alanine, glycine and serine; and phenylalanine, tryptophan and tyrosine are defined herein as biologically functional equivalents. To effect more quantitative changes, the hydropathic index of amino acids may be considered. Each amino acid has been assigned a hydropathic index on the basis of its hydrophobicity and charge characteristics, which are as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein, and correspondingly a polyamino acid, is generally understood in the art. It is known that certain amino acids may be substituted for other amino acids having a similar hydropathic index or score and still retain a similar biological activity. In making changes based upon the hydropathic index, the substitution of amino acids whose hydropathic indices are within 2 is preferred, those which are within approximately 1 are particularly preferred, and those within approximately 0.5 are even more particularly preferred.

It is also understood in the art that the substitution of like amino acids can be made effectively on the basis of hydrophilicity. As disclosed in U.S. Pat. No. 4,554,101, the following hydrophilicity values have been assigned to amino acid residues: arginine (+3.0); lysine (+3.0); aspartate (+3.0±1); glutamate (+3.0±1); serine 5 (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred.

Substitutions in a given OFA epitope are not limited to naturally and non-naturally occurring amino acids. Certain mimetics that mimic elements of protein secondary structure may be used. The underlying rationale behind the use of peptide mimetics is that the peptide backbone of proteins, including polyamino acids, exists chiefly to orientate amino acid side chains in such a way as to facilitate molecular interactions, such as those of antibody and antigen. A peptide mimetic is thus designed to permit molecular interactions similar to the natural molecule. Some successful applications of the peptide mimetic concept have focused on mimetics of β-turns within proteins, which are known to be highly antigenic. Likely α-turn structure within a polypeptide can be predicted by computer-based algorithms. Once the component amino acids of the turn are determined, mimetics can be constructed to achieve a similar spatial orientation of the essential elements of the amino acid side chains.

In addition to the 20 "standard" amino acids provided through the genetic code, modified or unusual amino acids as shown in table 1 can also be used in the present invention.

TABLE 1

| Modified and Unusual Amino Acids | | | |
|---|---|---|---|
| Abbr. | Amino Acid | Abbr. | Amino Acid |
| Aad | 2-Aminoadipic acid | EtAsn | N-Ethylasparagine |
| bAad | 3-Aininoadipic acid | Hyl | Hydroxylysine |
| bAla | beta-alanine, beta-Aminopropionic acid | aHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Flydroxyproline |
| | 6-Aminocaproic acid | Ide | Isodesmosine |
| Aep | | | |
| Ahe | 2-Aminoheptanoic acid | alle | allo-Isoleucine |
| Aib | | | |
| bAib | | | |
| | 2-Aminoisobutyric acid | MeGly | N-Methylglycine, sarcosine |
| | 3-Aminoisobutyric acid | MeIle | N-Methylisoleucine |
| Apm | 2-Aminopimelic acid | MeLys | 6-N-Methyllysine |
| Dbu | | | |
| | 2,4-Diaminobutyric acid | MeVal | N-Methylvaline |
| Des | Desmosine | Nva | Norvaline |
| Dpr | 2,3-Diaminopropionic acid | Om | Omithine |
| EtGly | N-Ethylglycine | | |

The OFA epitopes of the present invention may be administered to treat or prevent any cancer in a mammal that is characterized by the presence of OFA. Tc cells recognize OFA epitopes bound to class I MHC molecules. In view of the variability in the MHC proteins from patient to patient, and the multitude of Tc clones, it is preferred to formulate a complex or "cocktail" of OFA epitopes that stimulate different clones of Tc cells. In some embodiments of the present invention, the composition containing the Tc epitope(s) may also contain one or more Th epitopes. Th cells recognize OFA epitopes that are bound to MHC class II proteins, which again may vary from patient to patient. The stimulation of both CD4+ Th cells and CD8+ Tc cells may provide a greater immunogenic effect than the use of Tc epitope(s) alone. See, Zeng, J. Immunother. 24:195-204 (2001). The cocktail may be administered in several forms. In some embodiments, they are formulated as a mixture of peptides. In other embodiments, two or more epitopes are linked together to form a longer polypeptide that is amenable to synthetic (non-recombinant) synthesis e.g., a 20-60mer, thus including from about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to about 60 amino acids. In some preferred embodiments, the polypeptide contains about 50 amino acid residues. In these embodiments, it is preferred to use a linking agent that may be peptidic (e.g., about 3-5 amino acids in length) or non-peptidic in nature (e.g., a disulfide bridge). Determination of effective and optimal spacing between individual epitopes for purposes of binding with MHC proteins and identification by antigen processing cells may be determined in accordance with standard techniques.

In embodiments involving multiple OFA epitopes, administration can be facilitated by linking them to a common core structure such as a multi-branched lysine or arginine core to induce peptide specific CTL responses. (Tam, PNAS USA 85:5409-5413 (1988); Posnett et al., J. Biol. Chem. 263: 1719-1725 (1988)). Thus, in these embodiments where a plurality of Tc (and optionally one or more Th epitopes) are administered, e.g., contained in a given complex or cocktail, the composition will contain one or more (e.g., 2, 3, 4, 5, 6, 7, 8, 9, etc.) of the Tc epitopes e.g., epitopes containing OFA (53-60), OFA (81-88), OFA (148-155), OFA (156-163) and OFA (229-236), and optionally one or more, and preferably two or more Th epitopes e.g., epitopes containing OFA (152-161), OFA (229-238), OFA (241-250), OFA (253262), OFA (277-286) and OFA (285-294).

In yet other embodiments, the cocktail of epitopes is in the form of an OFA derivative that contains epitopes that stimulate Tc cells (and optionally one or more epitopes that stimulate Th cells) but that lack epitopes that stimulate Ts cells. For instance, an OFA derivative may differ from intact OFA in that it lacks any one or more, and preferably all Ts epitopes containing OFA (17-24), OFA (37-44), OFA (97-104) and OFA (140-147). Thus, the derivative may lack an entire region that contains multiple (overlapping and distinct) epitopes that stimulate Ts cells or it may lack one or more individual epitopes (e.g., those which have the highest affinity for Ts cells out of the epitopes that reside within the region of OFA). Regardless of the manner in which the OFA epitopes are administered, internalization and cellular processing of the epitopes in dendritic cells and presentation of antigenic peptide on the cell surface would be expected as shown in other systems. See, Ota, et al., Cancer Res. 62:1471-1476 (2002); Mattner, et al., Cancer Res. 62:1477-1480 (2002). Thus, the OFA epitopes may be used to inhibit growth or proliferation of a type of cancer, through enhancing a protective immune system response to OFA-bearing tumor cells (caused by preferential stimulation of Tc optionally with Th1 cells, relative to Ts cells), or to induce cancer immunity.

Cancer therapy in accordance with the present invention may be evaluated by monitoring the production of cytokines by the peripheral blood lymphocytes of the patient. One such method entails cytokine enzyme-linked immunospot (ELISPOT) assays in conjunction with computer-assisted image analysis after short in-vitro stimulation of the spleen cells (lymphocytes). Cytokines of interest include interferon-gamma, tumor necrosis factor alpha, IL-4, IL-5 and IL-10. For example, abnormally high levels of IL-10 would likely be indicative of relatively (and undesirably) high levels of CD8 T suppressor cells, indicative of immune suppression. On the other hand, immune enhancement and effective therapy would likely be evidenced by high levels of CD8 cells secreting interferon gamma and tumor necrosis factor alpha.

The OFA epitopes and derivatives of the present invention may be produced using a solid-phase peptide synthesis technique or via recombinant DNA technology by incorporating a DNA encoding the epitope into an appropriate expression vector, transforming a host via the vector, culturing the host (typically a bacterium such as *E. coli*) and isolating the expression product therefrom. The DNA sequence of full length OFA is attached hereto. Thus, it contains the sequences encoding the epitopes. Persons skilled in the art will appreciate that polynucleotides encoding the epitopes other than the sequences disclosed herein can be prepared e.g., to accommodate codon preference of a given host, in view of the degeneracy of the genetic code. See, e.g., Watson, et al., *Recombinant DNA,* 2nd Ed., Freeman, N.Y. (1993). Likewise, the nucleotide sequence of a given OFA derivative may be easily prepared (e.g., by deleting from the full length sequence the sequences encoding the aforementioned regions or epitopes). Synthetic schemes are preferred. The OFA analogs may be purified in accordance with standard techniques such as reverse-phase HPLC.

The OFA epitopes of the present invention may be formulated into pharmaceutical preparations for administration via any desired route e.g., subcutaneously, intravenously or intramuscularly, although intradermally or mucosally is preferred. Intradermal and mucosal administration are advantageous from the standpoints of lower doses and rapid absorption respectively. Mucosal routes of administration include oral, rectal and nasal administration. Preparations for mucosal administrations are suitable in various formulations as described below. The route of administration can be varied during a course of treatment. Variables such as dosage amounts, and timing and mode of administration will vary depending on several factors including the weight and overall health of the patient as well as the state of the disease. In some embodiments, the OFA analogs are administered in an amount of from about 5 μg to about 50 μg, given every two weeks for about 6½ weeks.

If the OFA epitope is water-soluble, it may be formulated in an appropriate buffer such as phosphate buffered saline or other physiologically compatible solutions. If on the other hand, the OFA analog has poor solubility in aqueous solvents, it may be formulated with a non-ionic surfactant such as TWEEN®, or polyethylene glycol. Thus, the OFA epitopes may be formulated for administration by inhalation or insufflation (either through the mouth or the nose) or oral, buccal, parenteral, rectal administration or, in the case of tumors, directly injected into a solid tumor. For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Preparations for oral administration may be suitably formulated to give controlled release of the OFA analog(s). Such compositions-may take the form of tablets or lozenges formulated in conventional manner.

For administration by inhalation, the OFA epitopes may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the OFA epitopes and a suitable powder base such as lactose or starch.

The OFA epitopes may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. The complexes may also be formulated in rectal compositions such as suppositories or retention enemas, e.g., containing conventional suppository bases such as cocoa butter or other glycerides. In addition to the formulations described previously, the OFA epitopes may also be formulated as a depot preparation. Such long acting formulations may be administered by implantation (for example, subcutaneously or intramuscularly) or by intramuscular injection. Thus, for example, the OFA epitopes may be formulated with suitable polymeric or hydrophobic materials (for example, as an emulsion in an acceptable oil) or ion exchange resins, or as sparingly soluble derivatives, for example, as a sparingly soluble salt. Micelles, liposomes and emulsions are well known examples of delivery vehicles or carriers for hydrophilic drugs, and are suitable delivery vehicles for the OFA epitopes of the present invention. The compositions may, if desired, be presented in a pack or dispenser device that may contain one or more unit dosage forms containing the noncovalent complexes. The pack may for example comprise metal or plastic foil, such as a blister pack. The pack or dispenser device may be accompanied by instructions for administration.

The immunogenic or immunotherapeutic compositions of the present invention contain a carrier in which the OFA/iLRP peptides can be suspended and, in general, allow a slow release of the OFA/iLRP to induce a longer period of immunization. The immunogenic compositions of the present invention will also typically contain an adjuvant. In preferred embodiments, the carrier also functions as an adjuvant. Freunds adjuvant (IFA) has been used in human immunotherapy against melanoma involving gp 100 peptide immunization (Rosenberg, S. A., J. C. Yang, D. J. Schwartzentruber, et al. 1998, *Nat. Med.* 4:321)). However, this adjuvant is not widely used in human vaccination protocols due to its undesirable side effects, such as erythema and induration at the injection site. Microfluidized (MF) 59 is an emulsion consisting of 5% (v/v), squalene, 0.5% (v/v), Tween 80, and 0.5% (v/v) Span 85 in water. It has been reported that the addition of MF59 adjuvant emulsion to conventional subunit influenza antigen causes enhanced immunogenicity without any clinically significant increase of reactogenicity (R. Gasparini. T. Pozzi, E. Montomoli 2001, 17, 135-40). See, also Podda, A. 2001, *Vaccine* 19:2673.

Unmethylated CpG dinucleotides in a certain base context (CpG motifs) contained in synthetic oligodeoxynucleotides (ODN) stimulate B cells and NK cells (Krieg, A. M., A. K. Yi, S. Matson, T. J. Waldschmidt, et al. 1995. CpG motifs in bacterial DNA trigger direct B-cell activation. *Nature* 374: 546)). They also activate dendritic cells (DCs) and induce maturation of DCs into professional antigen presenting cells (APCs) (Sparwasser, T., E. S. Koch, R. M. Vabulas, et al. 1998. *Eur. J. Immunol.* 28:2045; Hartmann, G., G. J. Weiner, A. M. Krieg. 1999, *Proc. Natl. Acad. Sci. USA* 96:9305; Sparwasser, T., R. M. Vabulas, B. Villmow, et al. 2000, *Eur. J. Immunol.* 30:3591; Vabulas, R. M., H. Pircher, G. B. Lipford, et al. 2000, *Immunol.* 164: 2372), thereby enhancing their ability to stimulate antigen-reactive T cells in vitro and in vivo. ODN-containing CpG motifs (referred to as CpG ODN) also stimulate macrophages to secrete Th1 cytokines, which are important in the development of a CTL response (Carson, D. A., E. Raz. 1997, 186:1621). In addition, CpG ODN have been shown to behave as adjuvant of Ab and CTL response directed against liposome-entrapped whole protein or class I-restricted peptides (Lipford, G. B., M. Bauer, C. Blank, et al. 1997. *Eur. J. Immunol.* 27:2340). Repeated administration of CpG ODN potentiates the CTL response against CTL peptide or protein emulsified in IFA and promotes the survival in response to tumor challenge in both prophylactic and therapeutic vaccination protocols (Davila, E., E. Celis. 2000, *J. Immunol.* 165:539). Evidence for the induction of a specific CTL response against a $CD8^+$ T cell peptide in the presence of CpG ODN without additional adjuvant has been reported by assessing the cytolytic activity of lymph node cells after in vitro stimulation (Vabulas, R. M., H. Pircher, G. B. Lipford, et. al. 2000, *J. Immunol.* 164:2372).

Cytokines such as fetal liver tyrosine kinase 3-ligand (Flt3-ligand or FL) that mobilize DCs in vivo will also expand various DC subsets in vivo (Pulendran, B., J. L. Smith, G. Caspary, et al. 1999, *Proc. Natl. Acad. Sci. USA* 96:1036; Shurin, M. R., P. P. Pandharipande, T. D. Zorina, et al. 1997. *Cell. Immunol.* 179:174). FL has been shown to expand distinct DC subsets in mice and to greatly augment antigen-specific T and B cell responses against soluble antigens and tumors (Pulendran, B., J. L. Smith, M. Jenkins, et al. 1998, *J. Exp. Med.* 188:2075; Lynch, D. H., E. Andreasen, E. Maraskovsky, et al. 1997, *Nat. Med.* 3:625). Dendritic cells have a unique ability to stimulate naive T cells. Recent evidence suggests that distinct DC subsets direct different classes of immune responses in vitro and in vivo. In humans, the monocyte-derived $CD11c^+$ DCs induce T cells to produce Th1 cytokines in vitro, whereas the $CD11c^-$ plasmacytoid T cell-derived DCs elicit the production of Th2 cytokines. Administration of either flt3-ligand (FL) or granulocyte-colony stimulating factor (G-CSF) to healthy human volunteers dramatically increases distinct DC subsets, or DC precursors, in the blood. FL increases both the $CD11c^+$ DC subset (48-fold) and the $CD11c^-$ $IL-3R^+$ DC precursors (13-fold). In contrast, G-CSF only increases the $CD11c^-$ precursors (e.g., greater than 7-fold). Freshly sorted $CD11c^+$ but not $CD11c^-$ cells stimulate $CD4^+$ T cells in an allogeneic MLR, whereas only the $CD11c^-$ cells can be induced to secrete high levels of IFN-alpha in response to influenza virus. $CD11c^+$ and $CD11c^-$ cells can mature in vitro with GM-CSF+TNF-alpha or with IL-3+ CD40 ligand, respectively. These two subsets up-regulate MHC class II co-stimulatory molecules as well as the DC maturation marker DC-lysosome-associated membrane protein. In addition, they stimulate naive, allogeneic $CD4^+$ T cells. These two DC subsets elicit distinct cytokine profiles in $CD4^+$ T cells, with the $CD11c^-$ subset inducing higher levels of the Th2 cytokine IL-10. The differential mobilization of distinct DC subsets or DC precursors by in vivo administration of cytokines such as FL and G-CSF also serves to manipulate immune responses in humans (B. Pulendran, et al., J. Immunol. 165:566-572 (2000)).

It has been further demonstrated that co-administration of type I interferon (IFN) with a human vaccine (influenza), causes a powerful adjuvant effect, inducing a Th1-type of immune response and protection against virus challenge (E. Proietti, et al., J. Immunol. 169:375-383 (2002)). When given intramuscularly, type I IFN was far superior to alum and was equivalent to complete freund's adjuvant (CFA), considered one of the most powerful adjuvants in animal models, as well as to MF59.

Yet other adjuvants contain polyinosinic acid-polycytidylic acid (poly(I-C)). The effect of this adjuvant on DC expression of IL-15 as well as the capacity of IL-15 to serve as a DC activator has been reported in Mattei, et al., J. Immunol. 167:1179-1187 (2000). Injection of poly(I:C) into mice induces up-regulated expression of both IL-15 and IL-15R alpha by splenic DCs. In addition, IL-15 treatment enhanced the expression of costimulatory markers on DCs, as well as their ability to stimulate antigen-specific CD8$^+$ T cell proliferation. Further, IFN-gamma secretion by splenic DCs was markedly increased after treatment with IL-15, suggesting that IL-15 modulates the ability of DCs to polarize T cell responses.

It is also preferred that the carrier contains an agent that activates (and thus causes maturation of) dendritic cells for optimal presentation of the OFA/iLRP peptides to T cells. The adjuvant may possess this property. As described above, unmethylated CpG oligodeoxynucleotides and poly (I:C) serve that purpose. Bacterial peptidoglycan and lipopolysaccharide activate dendritic cells as well. However, they need to be isolated and purified from bacteria. Thus, the methylated CpG oligodeoxynucleotides or polyinosinic acid:polycytidylic acid, are preferred for this purpose because as chemically synthetic carriers, they will activate dendritic cells so they can optimally present the OFA/iLRP peptides present in the carrier to T cells without having a potential disadvantage from the standpoint of microbial contamination.

As disclosed above, liposomes are suitable delivery vehicles for the OFA epitopes and derivatives of the present invention. Liposomes composed of natural or synthetic ester phospholipids (conventional liposomes) are known to be effective as immuno-adjuvants and as vaccine carriers (White, et al., Vaccine 13:1111-1122 (1995); Guan, et al., Bioconjugate Chem. 9:451-458 (1998)). A liposome-based vaccine against hepatitis A has been licensed for human use (Ambrosch, et al., Vaccine 15:1209-1213 (1997)). Sterically stabilized cationic liposomes (SSCL) have been used to significantly enhance the therapeutic efficacy of CpG ODN by increasing the bioavailability and duration of action of CpG ODN. Encapsulating CpG ODN in sterically stabilized cationic liposomes provides protection from serum nucleases while facilitating uptake by B cells, dendritic cells and macrophages. In an immunization model, coencapsulation of CpG ODN with protein antigen (Ag) magnified the Ag-specific IFN-gamma and IgG responses by 15- to 40-fold compared with Ag plus CpG ODN alone (Gursel, et al., J. Immunol. 167:3324-3328 (2001)).

There have been a number of approaches to improve the immuno-adjuvant action of liposomes, some of which involve modification of the liposome structure. Small size and positively charged carriers have been shown to be preferentially taken up by phagocytic cells such as DCs/macrophages and to elicit a significant CTL response. The mechanisms by which the liposomally encapsulated protein/peptide antigens are directed to the cytosol are believed to result from passive escape of the antigen from the endosomes into the cytoplasm where they access the MHC class I processing pathway (Zhou et al., Immunobiology 190:35-52 (1994)). However, a peptide sequence, referred to as antennapedia homeodomain (AntpHD), can effectively introduce CTL epitopes into the class I processing pathway and induce CTL in vivo. Chikh, et al., J. Immunol. 167:6462-6470 (2001), describes a vaccine which uses a recombinant peptide consisting of a CTL epitope, which binds MHC class I molecules, and a peptidic vector, AntpHD, that can deliver peptides into the cytosol of cells, where it is processed by the proteasome complex. The increase of the CTL response induced by AntpHD-fused peptide in liposomes correlates with this active transport to class I-processing pathway. Moreover, addition of CpG ODN immunostimulatory sequences further increase the CD8$^+$ T cell response. This strategy combining lipid-based carriers with antpHD peptide to target poorly immunogenic Ags into the MHC class I processing pathway represents a plausible approach for CTL vaccines that may have important applications for development of cancer vaccines.

Further, the unique ether glycerolipids of Archaea can be formulated into vesicles (archaeosomes) with strong adjuvant activity for MHC class I and class II presentation (Krishnan, J. Immunol. 165:5177-5185 (2000)). These investigators found that immunization of mice with ovalbumin (OVA) entrapped in archaeosomes resulted in a potent Ag-specific CD8$^+$ T cell response, as measured by IFN-gamma production and cytolytic activity toward the immunodominant CTL epitope OVA (aa 257-264). Interestingly, a long-term CTL response was generated with a low Ag dose even in CD4$^+$ T cell deficient mice, indicating that the archaeosomes could mediate a potent T helper cell-independent CD8$^+$ T cell response. Thus, delivery of proteins in self-adjuvanting archaeosomes represents a useful strategy for targeting exogenous antigens to the MHC class I pathway for induction of CTL response. Thus, several types of vesicles are useful as carriers for the immunotherapeutic agents of the present invention.

The OFA epitopes may be administered without an adjuvant. In certain embodiments, the epitopes are attached or conjugated to a lipophilic group and administered as a lipopeptide vaccine. See, Gahery-Segard, et al., J. Virol. 74:1694-1703 (2000); Gras-Masse, Mol. Immunol. 38:423-431 (2001); Vitello, et al., J. Clin. Invest. 95:341-349 (1995); BenMohamed, et al., Immunology 106:113-121 (2002); and Schild, et al., J. Exp. Med. 174:1665-1668 (1991) (reporting that an influenza virus lipopeptide without additional adjuvant elicited influenza virus-specific cytotoxic T (Tc) responses whereas the corresponding peptide without a lipid moiety did not). Examples of lipophilic groups include N-epsilon-palmitoyl-L-lysylamide and α-aminohexandecanoic acid. Peptides covalently attached to the N-epsilon-palmitoyl lysine moiety have been shown to activate macrophages and induce secretion of pro-inflammatory cytokines IL-1, IL-6, and TNF-α (Rouaix, et al., Vaccine 12:1209-14 (1994)). Lipopeptides also appear to target dendritic cells (Tsunoda, et al., Vaccine 17:675-685 (1999), which reported that in a comparative study with a bipalmitoylated peptide and its non-lipidic peptide analogue, immunohistological analysis of tissue from immunized mice revealed both macrophages and dendritic cell-associated lipopeptide, but not its non-lipidic analogue, and implicated dendritic cells in processing and presentation of lipopeptide particles to T cells). Dendritic cells, by contrast with macrophages, are unique in their capacity to prime naive T cells against soluble antigens administered in the absence of an adjuvant (Banchereau, et al., Nature 392:245-52 (1998)). It has become increasingly clear that manipulation of the immune response for vaccination purposes requires immunization routes allowing efficient antigen uptake by dendritic cells. (Mowat, Immunol. Lett. 65:133-40 (1999)). One study has shown that bone marrow-derived dendritic cells take up a model lipopeptide more efficiently than do macrophages (BenMohamed, et al., The Lancet Infect. Dis. 2:425-31 (2002)). Speculation is that this may be due to the palmitoyl moiety of lipopeptides fusing to lipid components of cell membranes and subsequently delivering the lipopeptides into the cytoplasm of dendritic cells (BenMohamed, et al., Vaccine 18:2843-55 (2000); Andrieu, et al., Eur. J. Immunol. 30:3256-65 (2000)). Besides binding and entering dendritic cells for presentation, lipopeptides have been shown to interact with Toll-like receptor 2 (Nishiguchi, et al., J. Immunol. 166:2610-16 (2001)) on the dendritic cell and so induce dendritic cell maturation which is required for optimal antigen presentation to T lymphocytes.

Modification of a peptide by attachment to lipophilic molecules, such as N-epsilon-palmitoyl-L-lysylamide or α-aminohexadecanoic acid (mono-palmitoyl peptide) can be achieved by conventional methods of peptide synthesis and characterization. See, Loing, et al., J. Immunol. 164:900-907 (2000); and Deprez, et al., Vaccine 14:375-382 (1996). For example, the lipid tail may be attached a posteriori by chemoselective ligation, which entails coupling of fully deprotected molecular fragments through two mutually and uniquely reactive functional groups. See, Gras-Masse, Mol. Immunol. 38:423-431 (2001). These approaches provide for scalable manufacturing and low cost synthetic vaccines. The lipopeptides produced by this methodology have been reported to induce as strong a CD8+ Tc cell response as the previously produced tri-palmitoyl lipopeptides (BenMohamed (2002), supra.). Also, such lipopeptides, have been reported to induce CD4+ Th cell responses (Pialoux, et al., AIDS 15:1239-49 (2001)). Mono-palmitoyl lipopeptides have been reported to be tolerated by the host with no local reaction to the synthetic lipopeptide vaccine (BenMohamed (2000), and Schild, et al., supra., and BenMohamed, et al., Immunol. 106:113-121 (2002)) in animal models and in human volunteers (Seth, et al., AIDS Res. Hum. Retroviruses 16:337-43 (2000c)). This mono-palmitoyl approach, therefore, appears to offer unique advantages in safety, cost, purity and simplicity of construction and obviates the need for toxic vaccine adjuvants (Gupta, et al., Vaccine 13:1263-76 (1995)).

In preferred embodiments, the vaccine composition of the present invention contains a plurality (i.e., two or more) lipopeptides, each of which contains a distinct Tc-inducing OFA epitope. In other preferred embodiments, the vaccine also contains one or more lipopeptides that contain a Th-inducing OFA epitope. The sequence of the epitopes will have to confirmed based on the HLA MHC proteins the patient expresses. Administration, e.g., intradermal or subcutaneous injection of this mixture of mono-palmitoyl-conjugated OFA/iLRP peptides will lead to uptake by and maturation of dendritic cells which then can present those peptides to Tc and Th cells in lymph nodes draining the site(s) of immunization. Thus, dendritic cells will be targeted in vivo by the lipopeptides.

There are many reasons why immunotherapy as provided by the OFA epitopes of the present invention is desired for use in cancer patients. First, if cancer patients are immunosuppressed, surgery with anesthesia and subsequent chemotherapy may worsen the immunosuppression. Appropriate immunotherapy in the pre-operative period using the compositions and methods of the present invention may prevent or reverse the immunosuppression. This could lead to fewer infectious complications and an accelerated wound healing. Second, tumor bulk is minimal following surgery; thus, immunotherapy is most likely to be effective in this situation. Third, tumor cells tend to be shed into the circulation as a result of surgery; thus, effective immunotherapy applied at this time can eliminate these cells. Preventive and therapeutic utilities of the present invention are directed to enhancing the immunocompetence of cancer patients before, during and/or after surgery, and to inducing tumor-specific immunity to cancer cells. While the ultimate clinical objective is total cancer regression and eradication, embodiments of the present invention are effective in inhibiting tumor growth and progression of the disease.

Compositions containing the OFA epitopes are useful in the prophylaxis or treatment of cancer in mammals. The cancers include but not limited to human lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia and heavy chain disease.

The therapeutic utility of the OFA epitopes and derivative of the present invention is not limited to in vivo uses. Mature dendritic cells express high levels of class I and class II MHC molecules, as well as high levels of various costimulatory molecules. Thus, dendritic cells are potent antigen-presenting cells for induction of T lymphocyte-mediated immunity. They can efficiently present MHC protein-bound antigenic peptides to T cells. The costimulatory molecules can complete the activation signalling of the antigenic peptide:MHC protein-induced T cells (Janeway, C. A., P. Travers, M. Walport, and M. Shlomchik. 2001. *Immunobiology: The Immune System in Health and Disease*. Garland Publishing, New York, pp. 307-309). In addition, the dendritic cells bring processed antigen from where it is encountered to the lymph nodes and spleen where immune responses are induced (Sallusto, et al., Arthritis Res. 4 Suppl. 3:S127-132 (2002)). Pure dendritic cells can be generated in vitro from a mammalian cancer patient's (e.g., human) peripheral blood monocytes (Nair, et al., Annals of Surgery 235:540-549 (2002)). For example, culturing peripheral blood mononuclear cells (monocytes) from a patient for 7-8 days with GM-CSF and IL-4, will cause differentiation of the monocytes into pure immature dendritic cells, and subsequent culture in the presence of medium containing double-stranded poly I:C RNA will induce dendritic cell maturation (Nair, supra., Holtl, et al., Clin. Cancer Res. 8:3369-76 (2002) (reporting on programming of dendritic cells using tumor cell lysate)). If desired, the autologous mature dendritic cells can be cryogenically preserved in liquid nitrogen for subsequent use with the patient from which they were derived.

The mature dendritic cells are cultured with one or more OFA/iLRP epitope(s) that specifically stimulate Tc cells, and optionally with one or more epitopes that specifically stimulate Th cells under conditions suitable to program the dendritic cells to potentiate T cell-mediated (anti-cancer) immunity e.g., for about 1 hour at about 37° C. The OFA epitopes can be added to the dendritic cells in medium or conjugated to a lipid adjuvant carrier (Zhou, et al., J. Immunother 25:289-

303 (2002)). The medium may also contain co-stimulants such as TNF-alpha, interleukins and prostaglandin. In general, the OFA epitope(s) are added to the medium in microgram amounts.

After dendritic cell loading of the OFA/iLRP peptides, the patient is administered the loaded dendritic cells. In one embodiment, the patient is administered about 3×10⁷ peptide-loaded dendritic cells via i.v. injection over 2-3 minutes, followed by intradermal administration of about 1×10⁶ OFA/iLRP epitope-loaded autologous dendritic cells in a volume of about 0.1 ml autologous plasma into the volar aspect of the forearm or thigh, every 4 weeks for four immunizations. Persons skilled in the art will appreciate that many variations of this treatment regimen would also be useful. A single dose of the loaded dendritic cells may provide a therapeutic benefit. Even if epitopes that are recognized by Ts cells are inadvertently present, dendritic cell presentation in vivo may actually overcome induction of those suppressive cells. Dendritic cell presentation of an autologous nuclear antigen actually breaks self-tolerance with activation of Th1 immunity and IgG antibody production in mice (Suen, et al., Immunol. 106:326-335 (2002)). Thus, immunization with OFA/iLRP epitope-loaded autologous mature dendritic cells may potentiate the immunity achieved with the immunotherapeutic compositions of the present invention alone.

The invention will be further described by reference to the following detailed examples. These examples are provided for purposes of illustration only, and are not intended to limit the scope of the invention described herein.

EXAMPLES

Summary of iLRP Epitopes Recognized by CD8⁺ Tc and Ts and CD4⁺ Th1 Clones from BALB/c Mice, and Experimental Protocol The epitopes recognized by 15 iLRP-reactive T cell clones derived from either naive BALB/c mice, BALB/c mice bearing MCA1315 fibrosarcoma tumors, or from BALB/c mice immunized with either 1 or 10 μg of recombinant murine iLRP were determined by testing the proliferation of those clones to overlapping peptides spanning the region of the iLRP molecule recognized by each clone in the presence of IL-2, as a growth factor for T cells and irradiated, T cell-depleted, syngeneic spleen cells as antigen-presenting cells. Proliferation was measured through ELISA determination of 5-bromodeoxyuridine incorporation during culture.

More specifically, the epitope-specificity of the iLRP-specific Th1, Tc, and Ts clones was determined using a modification of the 5'-bromodeoxyuridine (BudR) incorporation ELISA technique described in Rohrer, J. W., A. L. Barsoum, D. L. Dyess, J. A. Tucker, and J. H. Coggin, Jr. 1999. Human breast carcinoma patients develop clonable oncofetal antigen-specific effector and regulatory T lymphocytes. J. Immunol. 162:6880, using the Biotrak BUdR incorporation assay (Amersham, Arlington Heights, Ill.). Briefly, at the time of restimulation of the clones, a portion of the cloned T cells were assayed for proliferation to antigen-presenting cells (APC) and various iLRP peptides. The assay was performed with 10,000 viable cloned T cells/well plus 10⁵ irradiated syngeneic spleen cells (APC) plus 100 ng/well of intact iLRP/OFA protein or the various truncated iLRP/OFA proteins or the various iLRP/OFA peptides in Iscove's modified Dulbecco's medium (IMDM) containing 2 mM L-glutamine, 100 U/ml of penicillin G, 100 μg of streptomycin sulfate, and 10% fetal calf serum. The cells were cultured for a total of 48 hours. After 24 hours of culture 5'-bromodeoxyuridine was added to a final concentration of 10 μM/well. The cells were cultured for another 24 hours. At the end of the last 24 hours of incubation, the plates were centrifuged at 300×g for 10 min, and the labelling medium removed. The cells were then dried at 60° C. for 1 hour. The cells were fixed with an ethanol fixative provided in the Biotrak kit for 30 min at room temperature, fixative was removed, and the wells were coated with blocking buffer (1% protein in 50 mM Tris-HCl, 150 mM NaCl, pH 7.4) and incubated for 30 min at room temperature. The blocking buffer was removed, 100 μl of 1:100 diluted peroxidase-labelled anti-BUdR antibody was added to each well and the plates were incubated for 90 min at room temperature. The antibody solution was removed, and the wells washed three times with 300 μl/well of wash buffer. 200 μl of 3,3', 5,5'-tetramethylbenzidine in 150 (v/v) DMSO was added to each well and the plate was covered and incubated at room temperature while oscillating gently for 5-30 min. When the required color density was reached, the reaction was stopped by adding 25 μl of 1M sulfuric acid to each well and the plate read on a microELISA reader at 450 nm.

Each time the assay was done, clones were stimulated by APC and intact iLRP/OFA as a positive control. Cloned T cells were also cultured in the presence of only APC in IMDM or in the presence of APC and an iLRP/OFA peptide or truncated iLRP/OFA known not to stimulate the clones being tested. These served as negative controls. In wells where BUdR was incorporated (the iLRP/OFA stimulates proliferation of the T cells), the A450 was at least 10-fold and often approximately 50-fold higher than the negative controls. Because the Ts cells always presented with apparently low affinity T cell antigen receptors, their BUdR incorporation gave A450 values about 10 times higher than the negative controls (e.g., about 0.2 vs. 0.02), but about 5 times lower than the Th1 or Tc clones (e.g., usually about 0.9).

Determination of the portion of the truncated iLRP/OFA protein or peptide reacted to by a given clone was done by analysis of the proliferation pattern to the various truncated proteins or peptides. It was then determined what amino acid sequence was shared by those iLRP-truncated proteins or peptides that stimulated a T cell clone to proliferate.

Table 2 below shows the distribution of epitopes for the various types of T cell clones established, deduced on the basis of maximal response. Even though the cytotoxic T (Tc) cells and the IL-10-secreting Ts cells are both CD8 T cells and are both class I MHC-restricted, these two types of T cells recognize distinct epitopes on OFA. (SEQ ID NOS 6, 7, 9, 10, 8, 22-25, 25, and 15-20, respectively, in order of appearance)

TABLE 2

| iLRP-specific T Cell Clone | T Cell Type | iLRP Epitope Amino Acid Region | iLRP Epitope Sequence |
|---|---|---|---|
| M3 | Tc | 53-60 | RTWEKLLL |
| L6 | Tc | 81-88 | NTGQRAVL |
| L5 | Tc | 148-155 | CNTDSPLR |
| L4 | Tc | 156-163 | YVDIAIPC |
| L2 | Tc | 229-236 | GEWTAPAP |
| L1 | Ts | 17-24 | KLLAAGTH |
| H5 | Ts | 37-44 | YIYKRKSD |
| M11 | Ts | 97-104 | TPIAGRFT |
| H2 | Ts | 140-147 | VNLPTIAL |
| H4 | Ts | 140-147 | VNLPTIAL |
| H3 | Th1 | 152-161 | SPLRYVDIAI |
| NC1 | Th1 | 229-238 | GEWTAPAPEF |
| L3 | Th1 | 241-250 | AQPEVADWSE |
| M2 | Th1 | 253-262 | QVPSVPIQQF |
| H1 | Th1 | 277-286 | SAAPTAQATE |
| NC4 | Th1 | 285-294 | TEWVGATTDW |

Specificity Analysis of Various Types of iLRP-Reactive T Cell Clones.

Specificity of TS clone L1 using N-terminal peptides

Overlapping 12mer peptides of the first 25 amino acids of murine iLRP were produced. Thus, peptides 1-4 corresponded to amino acid residues 1-12, 5-16, 9-20 and 17-28 of murine iLRP. L1 is a BALB/c mouse CD8 Ts clone that was established from spleens of mice immunized twice at 2-week intervals with OFA/iLRP-conjugated nitrocellulose particles (i.e., a total OFA/iLRP dose each i.p. injection of 1 mcg). The spleens were harvested 2 weeks after the last immunization and the spleen cells were minced and washed by centrifugation, then cultured with $10^5$ irradiated MCA1315 fibrosarcoma tumor cells for two weeks in the presence of IL-2, IL-6, and interferon-gamma. The cells were then cloned by limiting dilution at 0.2 tumor-reactive T cells/well in the presence of $10^5$ irradiated, syngeneic spleen cells and $10^5$ irradiated, syngeneic MCA1315 fibrosarcoma cells in medium containing recombinant murine IL-2, recombinant murine IL-6, and recombinant murine IFN-gamma using the method described in Rohrer et al., 1995, *J. Immunol.* 154:2266. Results are shown in Table 3. (SEQ ID NOS 26-29, respectively, in order of appearance)

TABLE 3

BUdR Incorporation ($A_{450}$) of iLRP-specific T cell clone L1 cells after exposure to various iLRP-derived peptides.

| Stimulant | iLRP a. a. sequence | Expt. 1 | Expt. 2 |
|---|---|---|---|
| Medium | | .007 | .009 |
| iLRP truncated protein 13 | a. a.'s 242-295 | .016 | .014 |
| intact iLRP | a.a.'s 1-295 | .20 | .23 |
| Peptide 1 | MSGALDVLQMKE | .018 | .020 |
| Peptide 2 | LDVLQMKEEDVL | .017 | .019 |
| Peptide 3 | QMKEEDVLKLLAA | .09 | .07 |
| Peptide 4 | KLLAAGTHLGGT | .28 | .27 |

Clone L1 proliferates to a peptide contained almost entirely in peptide 4, but does react somewhat to peptide 3 as well, but a tetrapeptide that is common to both. The epitope that will maximally stimulate the L1 clone is deduced as KLLAAGTH (SEQ ID NO: 22). Results of an analysis of the specificity of iLRP-specific T cell clones reactive to iLRP peptide spanning amino acid residues 26-61 are shown in Table 4.

TABLE 4

| | CD8 T Cell Clones | |
|---|---|---|
| Stimulant | M3 (Tc) | H5 (Ts) |
| Medium | .008, .009 | .005, .007 |
| P15 (aa 81-92) | .018, .017 | .017, .018 |
| intact iLRP | .27, .30 | .23, .26 |
| P1 (aa 25-36) | .017, .02 | .017, .016 |
| P2 (aa 29-40) | .02, .021 | .016, .018 |
| P3 (aa 33-44) | .017, .019 | .23, .25 |
| P4 (aa 37-48) | .02, .018 | .22, .25 |
| P5 (aa 41-52) | .018, .021 | .017, .018 |
| P6 (aa 45-56) | .017, .021 | .021, .015 |
| P7 (aa 49-60) | .25, .28 | .019, .016 |

TABLE 4-continued

| | CD8 T Cell Clones | |
|---|---|---|
| Stimulant | M3 (Tc) | H5 (Ts) |
| P8 (aa 53-64) | .27, .30 | .017, .018 |
| P9 (aa 57-68) | .018, .021 | .017, .016 |

It appeared that clone M3 was responding to an epitope between amino acids 49 and 64 while clone H5 was responding to an epitope between amino acids 33 and 48. Once again, it appeared that distinct epitopes were being seen by Tc and Ts clones.

Analysis of Specificity of iLRP-specific T Cell Clones Reactive to iLRP Peptide Spanning Amino Acids 62-135

The same proliferation assay as described above was performed with CD8 cytotoxic T cell clone L6 and Ts clone M11. The results of the proliferation assay for clone L6 to iLRP deletion mutant truncated proteins showed that it recognized an epitope between amino acids 62 and 135 while the proliferation assay results to iLRP deletion mutant truncated proteins of clone M11 showed it responded to some epitope contained between amino acids 81 and 135. The proliferation assay results of these two clones to iLRP peptide 12-mers spanning the 62-135 amino acid region was conducted to define the epitopes for each clone and to determine if once again, the Tc and Ts cells recognized distinct epitopes. The results are shown in Table 5, and the deduced epitopes of the various clones are shown in Table 6.

TABLE 5

| | CD8 iLRP-specific T Cell Clones | |
|---|---|---|
| Stimulant | L6 (Tc) | M11 (Ts) |
| Medium | .007, .008 | .006, .008 |
| P3 (33-44) | .016, .017 | .015, .014 |
| Intact iLRP | .95, .96 | .21, .19 |
| P10 (aa 61-72) | .017, .017 | — |
| P11 (aa 65-76) | .015, .016 | — |
| P12 (aa 69-80) | .02, .015 | — |
| P13 aa 73-84) | .016, .018 | — |
| P14 (aa 77-88) | .96, .94 | .015, .017 |
| P15 (aa 81-92) | .95, .92 | .015, .016 |
| P16 (aa 85-96) | .02, .017 | .014, .017 |
| P17 (aa 89-100) | .015, .017 | .015, .016 |
| P18 (aa 93-104) | .017, .02 | .21, .18 |
| P19 (aa 97-108) | .015, .014 | .23, .15 |
| P20 (aa 101-112) | .016, .018 | .017, .02 |
| P21 (aa 105-116) | .02, .017 | .017, .014 |
| P22 (aa 109-120) | .02, .015 | .014, .016 |
| P23 (aa 113-124) | .015, .016 | .015, .016 |
| P24 (aa 117-128) | .016, .017 | .015, .017 |
| P25 (aa 121-132) | .017, .016 | .017, .015 |
| P26 (aa 125-136) | .016, .015 | .015, .018 |

(SEQ ID NOS 30-37, respectively, in order of appearance)

TABLE 6 iLRP Peptides That Induced T Cell Clone Proliferation

| P3 (aa 33-44) | QMEQYIYKRKSD |
|---|---|
| P4 (aa 37-48) | YIYKRKSDGTYI |
| P7 (aa 49-60) | INLKRTWEKLLL |
| P8 (aa 53-64) | RTWEKLLLAARA |

TABLE 6-continued iLRP Peptides That Induced T Cell Clone Proliferation

| | | |
|---|---|---|
| P14 | (aa 77-88) | ISSRNTGQRAVL |
| P15 | (aa 81-92) | NTGQRAVLKFAA |
| P18 | (aa 93-104) | ATGATPIAGRFT |
| P19 | (aa 97-108) | TPIAGRFTPGTF |

Clone H5 (a Ts clone) proliferated to iLRP peptides 3 and 4 equally well. The common sequence in those peptides is YIYKRKSD (SEQ ID NO: 23)(amino acids 37-44). Therefore, it was deduced that clone H5 recognizes that 8 amino acid iLRP epitope presented by a class I H-2d MHC protein.

Clone M3 (a Tc clone) proliferated to iLRP peptides 7 and 8 equally well. The common sequence in those peptides is RTWEKLLL (SEQ ID NO: 6)(amino acids 53-60). Therefore, it was deduced that that 8 amino acid sequence is the epitope presented by a class I H-2d MHC protein that is recognized by Tc clone M3. M3 must have a low affinity TCR because it proliferated no better to iLRP than did the Ts clones.

Clone L6 (a Tc clone) proliferated equally well to iLRP peptides 14 and 15. The common sequence of those peptides is NTGQRAVL (SEQ ID NO: 7) (amino acids 81-88). Therefore, it was deduced that that 8 amino acid sequence is the iLRP epitope presented by a class I H-2d MHC protein that is recognized by Tc clone L6.

Clone M11 (a Ts clone) proliferated equally well to iLRP peptides 18 and 19. The common sequence of those peptides is TPIAGRFT (SEQ ID NO: 24)(amino acids 97-104). Therefore, it was deduced that that 8 amino acid sequence is the iLRP epitope presented by a class I H-2d MHC protein that is recognized by Ts clone M11.

The question was posed whether clones which appear to be specific for a epitopes contained between amino acids 136 and 166 respond by proliferation to antigen-presenting cells presenting the processed 30mer which has the sequence of a.a.'s 136-166 of iLRP. To answer this question, the proliferation assay was done as above except that clones H3 (Th1), H2 and H4 ($T_S$), and L4 and L5 ($T_C$) were used. The results are shown in Table 7.

TABLE 7

BUdR incorporation ($A_{450}$) of iLRP-specific clones deductively determined to be reactive to epitopes within a. a.'s 136-166 when stimulated by that sequence or controls.

| Clone | Medium | Truncated iLRP protein 13 (a. a.'s 242-295) | intact iLRP | iLRP peptide (a. a.'s 136-166) |
|---|---|---|---|---|
| H3 (Th1) | .008 | .017 | .94 | .91 |
| H2 (Ts) | .008 | .015 | .26 | .24 |
| H4 (Ts) | .008 | .016 | .23 | .21 |
| L4 (Tc) | .007 | .017 | .89 | .90 |
| L5 (Tc) | .008 | .015 | .92 | .87 |

The clones whose reactivity patterns to the various truncated iLRP proteins suggested a specificity within amino acids 136-166, proliferate to the 30mer peptide which is the sequence of a.a.'s 136-166 (EASYVNLPTIALCNTDSPL-RYVDIAIPCNNK) (SEQ ID NO: 38). Although there was approximately a 4.5-fold difference between the BudR incorporation of the Th1 or Tc clone and the Ts clones, the data for the Ts clone are greater than 10-fold higher than the irrelevant iLRP peptide induced in any of the clones. The difference between the proliferation of the Th1 or Tc and the Ts clones was probably due to the T cell antigen receptor affinity for iLRP:self MHC. In previous experiments, using 75-100 ng/well of iLRP/OFA protein to stimulate proliferation, one dose was near the plateau of the dose response for the high affinity receptor-bearing Th1 and Tc clones, but just barely able to induce measurable proliferation ($^3$H-thymidine- or BUdR-incorporation) of the low-affinity receptor-bearing T cells (which was composed by some of the Th1 and Tc clones and all of the IL-10-secreting Ts clones).

Analysis of Additional Regions of Murine iLRP: Identification of Epitopes Contained Between Amino Acids 136 and 166

The BUdr incorporation assay for proliferation described for the assays above was used. The clones H3, H2, H4, L4, and L5 which proliferate in response to x-irradiated, syngeneic spleen cell-presented 30-mer iLRP peptide 136-166 in the presence of 100 U/ml of recombinant murine IL-2, were tested for their proliferation to overlapping 12-mer peptides covering the amino acid sequence of iLRP peptide 136-166. The results and the peptides used in the experiments are shown in Tables 8 and 9 respectively.

TABLE 8

BudR Incorporation ($A_{450}$) of T cell clones specific for iLRP peptide 136-166 to various peptides spanning that portion of iLRP protein.

| T Cell Clone | IMDM | Truncated iLRP Protein 13 (242-295) | Intact iLRP Protein (1-295) | iLRP peptide 31-1 (136-147) | iLRP peptide 31-2 (140-151) | iLRP peptide 31-3 (144-155) | iLRP peptide 31-4 (148-159) | iLRP peptide 31-5 (152-163) | iLRP peptide 31-6 (156-167) |
|---|---|---|---|---|---|---|---|---|---|
| H3 (Th1) | .007 | .015 | .88 | .016 | .015 | .016 | .81 | .95 | .03 |
| H2 (Ts) | .008 | .017 | .20 | .23 | .22 | .015 | .016 | .016 | .015 |
| H4 (Ts) | .008 | .018 | .21 | .22 | .24 | .017 | .016 | .016 | .016 |
| L4 (Tc) | .009 | .017 | .89 | .015 | .018 | .016 | .023 | .91 | .90 |

TABLE 8-continued

BudR Incorporation ($A_{450}$) of T cell clones specific for iLRP peptide 136-166 to various peptides spanning that portion of iLRP protein.

| | | | Stimulus | | | | | | |
|---|---|---|---|---|---|---|---|---|---|
| T Cell Clone | IMDM | Truncated iLRP Protein 13 (242-295) | Intact iLRP Protein (1-295) | iLRP peptide 31-1 (136-147) | iLRP peptide 31-2 (140-151) | iLRP peptide 31-3 (144-155) | iLRP peptide 31-4 (148-159) | iLRP peptide 31-5 (152-163) | iLRP peptide 31-6 (156-167) |
| L5 (Tc) | .007 | .016 | .90 | .017 | .016 | .90 | .89 | .024 | .015 |

TABLE 9

(SEQ ID NOS 39-44, respectively, in order of appearance)
Amino Acid Sequence of Overlapping 12-mer Peptides of iLRP 136-166 Peptide

| iLRP 12-mers | a.a. Range | a.a. Sequence |
|---|---|---|
| 31-1 | 136-147 | EASYVNLPTIAL |
| 31-2 | 140-151 | VNLPTIALCNTD |
| 31-3 | 144-155 | TIALCNTDSPLR |
| 31-4 | 148-159 | CNTDSPLRYVDI |
| 31-5 | 152-163 | SPLRYVDIAIPC |
| 31-6 | 156-167 | YVDIAIPCNNKG |

The Tc clone L4 proliferated to peptides 31-5 and 31-6 equally, so it was deduced that the sequence YVDIAIPC (SEQ ID NO: 10), which is common to both peptides, is an epitope specifically recognized by that clone on iLRP. Similarly, the equal proliferative response of Tc clone L5 to peptides 31-3 and 31-4 strongly suggested that an epitope specifically recognized by this clone is the sequence common to those two peptides (i.e., CNTDSPLR) (SEQ ID NO: 9). The Ts clones H2 and H4 both proliferated equally to peptides 31-1 and 31-2. Thus, it was deduced that both of those clones specifically recognize the 8-amino acid sequence common to those 2 peptides, namely VNLPTIAL(SEQ ID NO: 25). Regarding Th1 clone H3, the strongest response was to peptide 31-5 with a slightly lower response to 31-4. Therefore, it was deduced that the epitope having the sequence SPLRYVDIAI(SEQ ID NO: 15) was specifically recognized by clone H3. This sequence is entirely present in peptide 31-5, but peptide 31-4 lacks the last two amino acids of that peptide. The deduced epitopes that provide maximal stimulation to the T cell clones tested are set forth in Table 10.

TABLE 10

(SEQ ID NOS 15, 25, 25, 10 & 9, respectively, in order of appearance)
Proposed iLRP Epitopes for iLRP Peptide 136-166-reactive T Cell Clones

| T Cell Clone | Proposed iLRP Epitope | |
|---|---|---|
| H3 (Th1) | SPLRYVDIAI | (a.a. 152-161) |
| H2 (Ts) | VNLPTIAL | (a.a. 140-147) |
| H4 (Ts) | VNLPTIAL | (a.a. 140-147) |
| L4 (Tc) | YVDIAIPC | (a.a. 156-163) |
| L5 (Tc) | CNTDSPLR | (a.a. 148-155) |

Initially, 1 Th1, 2 Ts, and 2 Tc clones appeared to all respond to epitopes contained in the 30-mer iLRP peptide composed of amino acids 136-166. However, once the region was further analyzed using 12mer peptides spanning that 30mer region, distinct epitopes for the regulatory T cells and the effector T (Th1 and Tc) cells were found. The two Ts clones both responded to an epitope composed of amino acids 140-147 while the two Tc clones responded to epitopes composed of amino acids 148-155 and 156-163, respectively. The Th1 clone responded to an epitope that bridged the two Tc epitopes (amino acids 152-161). Thus, it was surprising to find the immuno-regulatory Ts clones responded to different epitopes than the Tc cells even though both types of cells are CD8, class I MHC-restricted iLRP-specific clones.

Analysis of Specificity of iLRP-specific Th1 Cell Clone Reactive to iLRP Peptide Spanning Amino Acids 168-242

As before, proliferation assays using ELISA measurement of BudR incorporation to measure proliferation of T cells cultured with various iLRP peptides and T cell-depleted, irradiated, syngeneic spleen cells as antigen presenting cells, all in medium containing 100 U/ml of IL-2 were done. The clones were with antigen-presenting cells and 100 ng/well of an irrelevant iLRP peptide as a negative control, intact iLRP protein as a positive control, or overlapping 12-mer iLRP peptides that spanned the 168-242 region of OFA. After 24 hours, BudR was added and the culture continued for another 24 hours, at which time, the cells were harvested and assayed for BudR incorporation as per the instructions of BioTrak Cell Proliferation ELISA System. The data presented below in Table 11 are the $A_{450}$ readings on the wells after the assay was complete. OFA epitopes are shown in Table 11a.

TABLE 11

Proliferation Results of Th1 Clone NC1 and Tc Clone L2 to iLRP Peptides

| Stimulant | Th1 Clone NC1 | Tc Clone L2 |
|---|---|---|
| Medium | .007, .008 | .008, .009 |
| P32 (aa 285-295) | .015, .017 | .016, .02 |

TABLE 11-continued

Proliferation Results of Th1 Clone NC1 and Tc Clone L2 to iLRP Peptides

| Stimulant | Th1 Clone NC1 | Tc Clone L2 |
|---|---|---|
| Intact iLRP | .24, .27 | .93, .91 |
| P1 (161-172) | .016, .015 | .015, .019 |
| P2 (165-176) | .017, .014 | .02, .018 |
| P3 (169-180) | .016, .014 | .017, .014 |
| P4 (173-184) | .015, .017 | .018, .02 |
| P5 (177-188) | .017, .016 | .014, .017 |
| P6 (181-192) | .015, .018 | .015, .016 |
| P7 (185-196) | .014, .017 | .016, .02 |
| P8 (189-200) | .015, .016 | .014, .02 |
| P9 (193-204) | .016, .018 | .017, .019 |
| P10 (197-208) | .014, .018 | .015, .017 |
| P11 (201-212) | .014, .017 | .014, .016 |
| P12 (205-216) | .018, .015 | .017, .015 |
| P13 (209-220) | .017, .015 | .017, .02 |
| P14 (213-224) | .015, .017 | .014, .016 |
| P15 (217-228) | .014, .016 | .015, .017 |
| P16 (221-232) | .016, .015 | .017, .02 |
| P16 (221-232) | .016, .015 | .017, .02 |
| P17 (225-236) | .16, .17 | .96, .94 |
| P18 (229-240) | .25, .28 | .95, .97 |
| P19 (233-244) | .015, .017 | .016, .018 |

TABLE 11a (SEQ ID NOS 45 & 46, respectively, in order of appearance)
iLRP Peptide Sequences Clones NC1 and L2 Recognize

| Peptide | Amino Acid Range | Sequence |
|---|---|---|
| P17 | aa 225-236 | EEFQGEWTAPAP |
| P18 | aa 229-240 | GEWTAPAPEFTA |

Class II MHC-bound peptides tend to vary in length between 8 and 30 amino acids. Most class II MHC-bound peptide epitopes are 9-11 amino acids in length; the length of the epitope recognized by Th1 clone NC1 was deduced to be 10 amino acids. Because the clone responded best to peptide 18, but significantly to peptide 17, it was deduced that clone NC1 recognized the epitope GEWTAPAPEF(SEQ ID NO: 16). Peptide 17 has all of that, but the last two amino acids E and F. The proliferation to even these peptides as well as to intact iLRP was lower than what was usually observed with Th cells. But the NC1 clone was derived from a mouse that had never been immunized with iLRP, but just had this clone present in its spleen. Therefore, it was a naive T cell, not a memory T cell, so its T cell antigen receptor had a lower affinity reaction with the iLRP peptide it recognized. Since CD8 Tc clone L2 proliferated identically to peptides 17 and 18, the deduced epitope for the L2 Tc clone was the common 8 amino acid sequence to both of those peptides, namely GEWTAPAP(SEQ ID NO: 8).

Analysis of Specificity of iLRP-specific Th1 Cell Clones Reactive to iLRP Peptide Spanning Amino Acids 243-295

As before, proliferation assays using ELISA measurement of BudR incorporation to measure proliferation of T cells cultured with various iLRP peptides and T cell-depleted, irradiated, syngeneic spleen cells as antigen presenting cells all in medium containing 100 U/ml of IL-2 were done. The cloned cells were cultured with antigen-presenting cells and 100 ng/well of an irrelevant iLRP peptide as a negative control, intact iLRP protein as a positive control, or overlapping 12-mer iLRP peptides that spanned the 243-295 region. After 24 hours, BUdR was added and the culture continued for another 24 hours, at which time, the cells were harvested and assayed for BUdR incorporation as per the instructions of BioTrak Cell Proliferation ELISA System. The data presented below in Table 12 are the $A_{450}$ readings on the wells after the assay was complete. Deduced epitopes are set forth in Table 13.

TABLE 12

Proliferation Results ($A_{450}$) of Th1 Clones to iLRP Peptides

| | Th1 Clones | | | |
|---|---|---|---|---|
| Stimulant | NC4 | M2 | H1 | L3 |
| Medium | .005, .008 | .007, .008 | .007, .005 | .008, .009 |
| P1 (161-172) | .017, .015 | .017, .018 | .015, .02 | .02, .015 |
| Intact iLRP | .23, .27 | .87, .91 | .95, .96 | .95, .98 |
| P19 (233-244) | .017, .014 | .017, .02 | .018, .02 | .019, .015 |
| P20 (237-248) | .015, .016 | .015, .019 | .019, .018 | .85, .83 |
| P21 (241-252) | .015, .016 | .018, .017 | .02, .02 | .96, .98 |
| P22 (245-256) | .015, .017 | .017, .016 | .019, .017 | .018, .02 |
| P23 (249-260) | .018, .014 | .81, .83 | .017, .016 | .02, .016 |
| P24 (253-264) | .017, .015 | .93, .95 | .016, .02 | .017, .016 |
| P25 (257-268) | .018, .014 | .018, .02 | .016, .02 | .017, .02 |
| P26 (261-272) | .015, .017 | .02, .015 | .02, .015 | .016, .019 |
| P27 (265-276) | .017, .014 | .015, .018 | .017, .015 | .015, .018 |
| P28 (269-280) | .015, .016 | .019, .02 | .016, .017 | .016, .018 |
| P29 (273-284) | .014, .016 | .02, .017 | .85, .83 | .014, .017 |
| P30 (277-288) | .015, .018 | .016, .017 | .96, .98 | .014, .02 |
| P31 (281-292) | .17, .15 | .016, .018 | .015, .019 | .02, .02 |
| P32 (285-295) | .28, .26 | .016, .02 | .02, .017 | .017, .018 |

TABLE 13

(SEQ ID NOS 47-54, respectively, in order of appearance)
iLRP Peptide Sequences Clones NC4, M2, H1, and L3 Recognize

| Peptide | Amino Acid Range | Sequence |
|---|---|---|
| P20 | aa 237-248 | EFTAAQPEVADW |
| P21 | aa 241-252 | AQPEVADWSEGV |
| P23 | aa 249-260 | SEGVQVPSVPIQ |
| P24 | aa 253-264 | QVPSVPIQQFPT |
| P29 | aa 273-284 | TEDWSAAPTAQA |
| P30 | aa 277-288 | SAAPTAQATEWV |
| P31 | aa 281-292 | TAQATEWVGATT |
| P32 | aa 285-295 | TEWVGATTDWS |

Since the clone NC4 responded best to peptide 32, but significantly to peptide 31, it was deduced that clone NC4 recognized the epitope TEWVGATTDW(SEQ ID NO: 20) (amino acids 285-294). Peptide 31 has all of that except the last two amino acids D and W. Like the proliferation of NC1 to intact iLRP or appropriate iLRP peptides, the proliferation of NC4 to these peptides as well as to intact iLRP was lower than what was observed with the other Th cells assayed. This is because both NC1 and NC4 were clones derived from normal mice and therefore, not memory T lymphocytes and so had lower affinity binding of iLRP. Because clone M2 responded best to peptide 24, but significantly to peptide 23, it was deduced that clone M2 recognized the epitope QVPSVPIQQF(SEQ ID NO: 18) (amino acids 253-262). Peptide 23 has all of that except the last two amino acids Q and F. Since clone H1 responded best to peptide 30, but significantly to peptide 29, it was deduced that clone H1 recognized the epitope SAAPTAQATE(SEQ ID NO: 19) (amino acids 277-286). Peptide 29 has all of that except the last two amino acids T and E. Since clone L3 responded best to peptide 21, but significantly to peptide 20, it was deduced that clone L3 recognized the epitope AQPEVADWSE(SEQ ID NO: 17) (amino acids 241-250). Peptide 20 has all of that except the last two amino acids S and E.

Confirmation of Peptide Epitope Binding to H-2d Class I Proteins.

Using a computer program developed by the University of Tuebingen, available through the internet for identification of potential binding epitopes based on the particular MHC motifs, the amino acid sequence of the OFA/iLRP 30mer peptide that contains amino acids 136-166 was checked for $L^d$-bound motifs. See Table 14. Of the epitopes for the Ts and Tc clones which have been shown to be reactive with this region, the results of the present analysis show that the same epitopes would be reactive with the $L^d$ class I molecule.

on the antigen-presenting cell. Since the T cell recognizes the other side of the sequence (epitope) in association with the MHC, high binding to the MHC indicates a greater likelihood of recognition of the epitope by the T cell. In these tables, the higher the binding score, the better the binding. Thus, The amino acid residues set forth in bold are important for binding of the agretope to the MHC. As per the disclosure above, embodiments of the present invention include combinations of 2 or more of the peptide sequences TIALCNTDS(SEQ ID NO: 11), TDSPLRYVD(SEQ ID NO: 12), PLRYVDIAIP (SEQ ID NO: 57) and PLRYVDIAIP(SEQ ID NO: 57), that when administered to a human, will stimulate Tc cells (and in the case of the peptides TDSPLRYVD(SEQ ID NO: 12) and PLRYVDIAIP(SEQ ID NO: 57), stimulate Th cells). Such combinations include 2 or more individual peptides linked together e.g., via a spacer comprised of amino acids, or linked to a common carrier.

The same 30mer sequence was analyzed in the same manner to identify peptides that would be bound by human HLA class I protein A-2 (genotype HLA-A*0201) as determined

TABLE 14

Reactive T cell clones & H2-Ld Anchor motif
(SEQ ID NOS 39-44, respectively, in order of appearance)

```
31-1  aa136-147   EASYVNLPTIAL                     Ts
31-2  aa140-151       VNLPTIALCNTD                 Ts
31-3  aa144-155           TIALCNTDSPLR             Tc
31-4  aa148-159               CNTDSPLRYVDI         Tc & TH1
31-5  aa152-163                   SPLRYVDIAIPC     Tc & TH1
31-6  aa156-167                       YVDIAIPCNNKG Tc

Binding Score
(SEQ ID NO: 39)
31-1              aa136-147   EASYVNLPTIAL   2   Ts
                              EASYVNLPTIAL  17   Ts
                              EASYVNLPTIAL   1   Ts
                              EASYVNLPTIAL  12   Ts (SEQ ID NO: 40)
31-2              aa140-151   VNLPTIALCNTD   2   Ts
                              VNLPTIALCNTD   2   Ts
                              VNLPTIALCNTD  15   Ts
                              VNLPTIALCNTD   1   Ts (SEQ ID NO: 41)
31-3              aa144-155   TIALCNTDSPLR   3   Tc
                              TIALCNTDSPLR   1   Tc
                              TIALCNTDSPLR  10   Tc
                              TIALCNTDSPLR   1   Tc (SEQ ID NO: 42)
31-4              aa148-159   CNTDSPLRYVDI   2   Tc & TH1
                              CNTDSPLRYVDI   2   Tc & TH1
                              CNTDSPLRYVDI   5   Tc & TH1
                              CNTDSPLRYVDI  17   Tc & TH1

(SEQ ID NO: 43)
31-5              aa152-163   SPLRYVDIAIPC  11   Tc & TH1
                              SPLRYVDIAIPC   6   Tc & TH1
                              SPLRYVDIAIPC   2   Tc & TH1

(SEQ ID NO: 44)
31-6              aa156-167   YVDIAIPCNNKG   2   Tc
                              YVDIAIPCNNKG   3   Tc
                              YVDIAIPCNNKG   3   Tc
                              YVDIAIPCNNKG   2   Tc
```

Using the same methodology, two additional OFA eptiopes that specifically stimulate Tc cells were identified, mainly OFA (58-66) (e.g., LLLAARAIV) (SEQ ID NO: 55) and OFA (60-68) (e.g., LAARAIVAI) (SEQ ID NO: 56).

In Table 14 (as well as in Table 15 below), binding score refers to one side of the epitope (agretope) to the MHC protein by the peptide motif required for binding by the HLA-A2 protein. This produced 24 9mer peptides that should be bound by HLA-A2 class I protein and so presented as epitopes to T cells. See Table 15. This means that, although the peptides that will serve as epitopes for mouse T cells of a given strain will not necessarily be the exact epitopes for either another MHC-disparate strain of mouse, or for humans, the same regions of the OFA/iLRP which are reactive with murine T cells will probably also be able to serve as a source of peptide epitopes of a slightly different sequence which will be recognized by human T cells. The peptides will be different for different MHC haplotypes to some extent and thus the exact epitopes recognized by T cells will be slightly different, but some epitopes may be seen by T cells of different individuals or species due to the high degree of OFA/iLRP amino acid sequence conservation.

TABLE 15

Anchor Motif for human HLA-A*0201 within aa136-aa166 peptide (SEQ ID NOS 58-82, respectively, in order of appearance) aa136 . . . aa166

| EASYVNLPTIALCNTDSPLRYVDIAIPCNNKG | Binding Score |
|---|---|
| EASYVNLPT | 5 |
| ASYVNLPTI | 18 |
| SYVNLPTIA | 7 |
| YVNLPTIAL | 21 |
| VNLPTIALC | 11 |
| NLPTIALCN | 11 |
| LPTIALCNT | 9 |
| PTIALCNTD | 7 |
| TIALCNTDS | 10 |
| IALCNTDSP | 12 |
| ALCNTDSPL | 22 |
| LCNTDSPLR | 4 |
| CNTDSPLRY | 1 |
| NTDSPLRYV | 19 |
| TDSPLRYVD | 4 |
| DSPLRYVDI | 9 |
| SPLRYVDIA | 13 |
| PLRYVDIAI | 15 |
| LRYVDIAIP | 9 |
| RYVDIAIPC | 1 |
| YVDIAIPCN | 11 |
| VDIAIPCNN | 3 |
| DIAIPCNNK | 11 |
| IAIPCNNKG | 13 |

Determination of OFA/iLRP Eptitopes for Use in Humans

First, take 4 heparinized tubes of blood from the patient and send one to the HLA typing laboratory to determine the HLA genotype of the patient. The 3 other tubes of heparinized blood are used as a source of T lymphocytes and antigen-presenting cells. The heparinized blood of the patient is pooled and the peripheral blood mononuclear leucocytes (PBML) is purified by density gradient centrifugation in Ficoll-Paque Plus (Pharmacia Biotech, Piscataway, N.J.) using a modification of the method of Boyum (Boyum, *Scand. J. Clin. Lab. Invest.* 21:97:S77 (1968)) as previously published and Rohrer et al., *J. Immunol.* 162:6880 (1999). The purified PBML is resuspended in RPMI-1640 medium and washed by centrifugation 3 times and then a viability count done using Trypan Blue dye exclusion.

Second, the counted PBML is diluted to $5\times10^6$ viable cells/ml in RPMI-1640 medium and then the cell suspension is split into two aliquots. (a) One aliquot of cells serves as the source of antigen-presenting cells in the proliferation assay. Deplete this aliquot of T cells by negative selection on anti-CD3 monoclonal antibody coated Petri plates using the method described in Wysocki et al., *Proc. Natl. Acad. Sci.* (*USA*) 75:2844 (1978), except that anti-CD3 antibody is used and that the anti-CD3 antibody is added and binds to the plates on the day of the cell separation. See Boyum, *Scand. J. Clin. Lab. Invest.* 21:97:S77 (1968). After incubation and removal of cells not adhering to anti-CD3-coated plates, the non-adherent cells (non-T cells) are washed by centrifugation in RPMI-1640 medium by centrifugation and X-irradiated at 3000 R to inhibit their ability to proliferate. After X-irradiation, they are counted for viability using Trypan Blue dye exclusion and kept on ice until the proliferation assay is done. (b) The aliquot of cells not used for $CD3^+$ cell (T cell) depletion is split in half and positively selected for CD4 T cells and CD8 T cells using magnetic cell sorting. One half of the cells are incubated on ice with magnetic beads that are conjugated with anti-human CD4 monoclonal antibody. The other aliquot is incubated with magnetic beads that are conjugated with anti-human CD8 monoclonal antibody. The incubations are done on ice for 45 minutes. One tube (the anti-CD4 tube) is put in the field of a Becton-Dickinson Imag magnet, and the cells to which the antibody-coated magnetic beads have bound will bind to the side of the side of the tube having the magnet. The supernatant containing the cells not bearing the marker to which the antibody binds is removed by pipetting. New medium is carefully added to the tube and the supernatant removed again. After the non-bound cells are removed, the magnet will be removed and the anti-CD4 antibody-conjugated magnetic bead-bound cells are released from the side of the tube. Those CD4 T cells are removed by pipetting, washed by centrifugation in medium, and counted for viability by Trypan Blue dye exclusion. The same separation procedure is done to obtain CD8 T cells using anti-human CD8 monoclonal antibody-conjugated magnetic beads. The two populations of T cells are diluted to $5\times10^6$ viable cells/ml.

Third, the CD4 T cells and the CD8 T cells are assayed for proliferation to intact OFA/iLRP or 12-mer peptides that overlap by 4 amino acids, but span the entire 295 amino acid sequence of OFA/iLRP (as was done to obtain the mouse epitope data presented in the examples above). The method described in Rohrer et al., *J. Immunol.* 162:6880 (1999) is used to assess proliferation. Ninety-six (96) well plates are used and 0.1 ml of irradiated T cell-depleted PBML (obtained using the method described in (a) above) are added to each well. That volume also contains 100 ng of intact OFA/iLRP, or a 12-mer peptide of OFA/iLRP. We then add 0.1 ml of CD4 or CD8 T cells from the cancer patient's peripheral blood (purified by the method described in the first paragraph of the example, and in (b) above to all wells. We use $5\times10^4$-$5\times10^5$ viable T cells/well, and incubate the plates containing the CD4 or CD8 T cells, irradiated antigen-presenting cells plus intact OFA/iLRP or OFA/iLRP 12-mer peptides for 48 hours at 37° C. in a humidified 95% air/5% $CO_2$ atmosphere. Twenty-four hours before harvest, 20 μl of 5-bromodeoxyuridine (BUdR) are added to yield a total concentration of 10 μM BUdR/well. The cell cultures are then returned to 37° C. in a humidified 95% air/5% CO₂ atmosphere for the remaining 24 hours. Proliferation will be assayed using the Biotrak BUdR incorporation assay (Amersham, Arlington Heights, Ill.) as described previously. After preparation and fixation of the labelled cells, precipitation of the cell DNA and enzyme-conjugated anti-BUdR antibody binding to the DNA, followed by washing and addition of a substrate for the enzyme that will produce a colored product, plates are analyzed by a microELISA reader and 450 nm absorbance measured. By analysis of the absorbance values compared to negative controls, we determine which OFA/iLRP peptides induced proliferation by the patient's CD4 and CD8 T cells specific for OFA/iLRP. These data allow determination of the OFA/iLRP epitopes recognized by the patient's T cells.

Fourth, because the cytotoxic T (Tc) cells and the IL-10-secreting, suppressor T (Ts) are both CD8 T cells and because induction of the Ts cells inhibits Tc cell killing of tumor cells (Rohrer, et al., *J. Immunol.* 155:5719 (1995)), it is determined which of the epitopes that induce proliferation of the cancer patient's CD8 T cells are inducing Tc and which are inducing Ts cell activation. The Tc cells secrete interferon-γ, but not IL-10 while the Ts cells secrete IL-10, but not interferon-γ. We set up some of the CD8 and CD4 T cell cultures as described above, in ELISPOT plates coated with either anti-interferon-γ or anti-IL-10 antibody. The mixture of irradiated, autologous antigen-presenting cells, CD4 or CD8 T cells, and intact OFA/iLRP or the same 12-mer OFA/iLRP peptides as in the proliferation assay are used. The cells are incubated at 37° C. in a humidified 95% air/5% CO₂ atmosphere for 24-48 hours. At the end of that time, the cells are washed off the wells and the biotinylated antibody (anti-interferon-γ or anti-IL-10) is added, incubated for 12 hours at 4° C., and then each well is washed to remove unbound antibody. This is followed by a 2-hour incubation with either streptavidin-alkaline phosphatase or horseradish peroxidase at room temperature. The appropriate substrate for the enzyme on the streptavidin is added, incubated at room temperature for 5-30 minutes, the reaction stopped and the spots resulting from cytokine secretion and being bound to the membrane bottom of the well are counted using a Becton-Dickinson Immunospot Analyzer. By combining the proliferation assay data with the ELISPOT data, the OFA/iLRP peptides induce CD8 Tc cells (interferon-γ-secreting) and the peptides that induce CD8 Ts cells (IL-10-secreting) are identified. The same analysis of CD4 T cells allows a determination of whether different class II HLA-presented peptides induce CD4 Th1 cells rather than CD4 Th2 cells. If they do, cell-mediated immunity against the tumor is augmented by immunizing only with Th1-inducing OFA/iLRP peptides.

Once these data are obtained, resort is made to the database of HLA anchor motifs to determine which class I HLA protein is responsible for presenting the peptides that are desired to be used. At this point, the HLA genotype of the patient and sequence of the OFA/iLRP peptides that induce T cell proliferation and interferon-γ-secretion are known. After this analysis is done on enough patients, a large enough bank of data telling which peptides need to be used for immunization in a patient with a given HLA haplotype is accumulated. Thus, for a given HLA haplotype, there is a given set of OFA/iLRP peptides that induces effective immunotherapy of the tumor.

INDUSTRIAL APPLICABILITY

The present invention has applicability in cancer medicine and research.

All publications cited in the specification (e.g., the list of citations below) are indicative of the level of skill of those skilled in the art to which this invention pertains. All these publications are herein incorporated by reference to the same extent as if each individual publication were specifically and individually indicated to be incorporated by reference. In addition, Applicants' provisional patent application No. 60/400,851, filed Aug. 2, 2002, is incorporated herein by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

LIST OF CITATIONS

1. Astrow, A. B., Lancet 343:494 (1994).
2. Bailar J. C., et al., N. Engl. J. Med. 314:1226 (1986)
3. Gallagher, H. S., et al., Cancer 23:855 (1969)
4. Sprat, J. S., et al., Cancer Res. 46:970 (1986)
5. Zhuang, A., et al., Cancer Res. 55:467 (1995).
6. Leffel, M. S., et al., Cancer Res. 37:4112 (1977).
7. Coggin, J. H., Jr., Mol. Biother. 1:223 (1989).
8. Van den Eynde, B. J., et al., Curr. Opinion Immunol. 9:684 (1997).
9. Melief, C., et al., Immunol. Rev. 145:167 (1995).
10. Breenberg, P. D., et al., Adv. Immunol. 49:281 (1991).
11. Coulie, P. G., et al., J. Immunother. 14:104 (1993).
12. Hellstrom, I., et al., Crit. Rev. Immunol. 18:1 (1998).
13. Nabeta, Y. Mod., Asp. Immunobiol. 1:17 (2000).
14. Coggin, J. H., Jr., et al., Immunol. Today 19:405 (1998).
15. Seiter, S., et al., Mod. Asp. Immunobiol. 1:121 (2000).
16. Landowski, T. H., et al., Biochem. 34:11276 (1995).
17. Castronovo, V., Invasion Metastasis 13:1 (1993).
18. van den Brule, F. A., et al., Biochem Biophys. Res. Commun. 201:388 (1994).
19. Menard, S., et al., Biochem. 67:155 (1997).
20. Coggin, J. H., Jr., et al., Anticancer Res. 19:1 (1999).
21. Liotta, L. A., et al., Prog. Clin. Biol. Res. 256:3 (1988).
22. Azavoorian, S., et al., Cancer 71:1368 (1993).
23. Terranova, V. P., et al., Cancer Res. 42:2261 (1982).
24. Terranova, V. P., et al., Science 226:982 (1984).
25. Ardini, E., et al., J. Biol. Chem. 272:2342 (1997).
26. Romanov, V., et al., Cell Adhes. Commun. 2:201 (1994).
27. Turpeeniemi, H. T., et al., J. Biol. Chem. 261:1883 (1986).
28. Sweeney, T. M., et al., Cancer Metastasis Rev. 10:245 (1991).
29. D'Erico, A. S., et al., Mol. Pathol. 4:239 (1991).
30. Monteagudo, C. M., et al., Am. J. Pathol. 136:585 (1990).
31. Grigoni, W. F., et al., Am. J. Pathol. 138:647 (1991).
32. Sobel, M. E., Semin. Cancer Biol. 4:311 (1993).
33. Martignone, S., et al., J. Natl. Cancer Inst. 85:398 (1993).
34. Waltregny, D., et al., J. Natl. Cancer Inst. 89:1224 (1997).
35. Pellegrini, R., et al., Breast Cancer Res. Treat. 35:195 (1995).
36. Menard, S., et al., Br. J. Cancer 69:1126 (1994).
37. Vollmers, H. P., et al., FEBS Letters 172:17 (1984).
38. Wu, S. Chung-hua Ping L1 Hsuch Tsa Chih 22:207 (1993).

39. Terranova, V. P., et al., Cancer Res. 42:2265 (1982).
40. Rohrer, J. W., et al., J. Immunol. 154:2266 (1995).
41. Coggin, J. H., Jr., et al., Am. J. Pathol. 130:136 (1988).
42. Rohrer, J. W., et al., J. Immunol. 155:5719 (1995).
43. Coggin, J. H., Jr., et al., Int. J. Rad. Biol. 71:81 (1997).
44. Rohrer, J. W., et al., J. Immunol. 162:6880 (1999).
45. Zelle-Reiser, C., et al., J. Urol. 165:1705 (2001).
46. van den Brule, F. A., et al., Hum. Pathol. 27:1185 (1996).
47. Payne, W. J., Jr., et al., J. Natl. Cancer Inst. 75:527 (1985).
48. Gussack, G. S., et al., Cancer 62:57.
49. Rohrer, J. W., et al., Mod. Asp. Immunobiol. 1:191 (2001).
50. Rao, et al., Biochemistry 28:7476-7486 (1989).
51. Yow, et al., Proc. Natl. Acad. Sci. USA 85:6394-6398 (1988).
52. Coggin, et al., Anticancer Res. 19:5535-5542 (1999).
53. Van den Brule, et al., Biochem. Biophys. Res. Commun. 201:388-3993 (1994).
54. Coggin, et al., Arch. Otolaryngol Head Neck Surg. 119: 1257-1266 (1993).

The invention claimed is:

1. A method of autologous cancer therapy, comprising:
culturing monocytes collected from a cancer patient in the presence of IL-4 and GM-CSF to allow differentiation of the monocytes into immature dendritic cells;
culturing the dendritic cells in the presence of at least one oncofetal antigen (OFA) epitope that selectively stimulates T cytotoxic lymphocytes, and optionally at least one co-stimulant, to produce programmed dendritic cells, wherein the culturing is not conducted in the presence of an OFA epitope that specifically stimulates T suppressor cells; and
administering the programmed dendritic cells to the cancer patient.

2. The method of claim 1, wherein culturing of (b) includes the at least one co-stimulant which comprises TNF-alpha, an interleukin and prostaglandin.

3. The method of claim 1, wherein the culturing of (b) includes at least one OFA epitope that selectively stimulates T helper lymphocytes.

4. The method of claim 1, further comprising preserving the programmed dendritic cells in liquid nitrogen prior to the administering.

5. The method of claim 1, wherein the administering comprises intravenous injection of about $3 \times 10^7$ programmed dendritic cells, followed by intradermal administration of about $1 \times 10^6$ programmed dendritic cells into the volar apsect of the forearm or thigh of the cancer patient, once per week for 4 weeks.

6. The method of claim 1, wherein the administering comprises a single dose of the programmed dendritic cells.

7. The method of claim 1, wherein the at least one OFA epitope that specifically stimulates T cytotoxic lymphocytes is selected from the group consisting of RTWEKLLL (SEQ ID NO:6), NTGQRAVL (SEQ ID NO:7), CNTDSPLR (SEQ ID NO:9), YVDIAIPC (SEQ ID NO:10), and GEWTAPAP (SEQ ID NO:8), and mixtures thereof.

8. The method of claim 3, wherein the at least one OFA epitope that specifically stimulates T helper lymphocytes is selected from the group consisting of SPLRYVDIAI (SEQ ID NO:15), GEWTAPAPEF (SEQ ID NO:16), AQPEVADWSE (SEQ ID NO:17), QVPSVPIQQF (SEQ ID NO:18), SAAPTAQATE (SEQ ID NO:19), and TEWVGATTDW (SEQ ID NO:20), and mixtures thereof.

9. A method of autologous cancer therapy, comprising:
administering programmed autologous dendritic cells to a cancer patient, wherein the autologous dendritic cells were prepared by culturing monocytes collected from the cancer patient in the presence of IL-4 and GM-CSF to allow differentiation of the monocytes into immature dendritic cells; and culturing the dendritic cells in the presence of at least one oncofetal antigen (OFA) epitope that selectively stimulates T cytotoxic lymphocytes, and optionally at least one co-stimulant, to produce programmed dendritic cells, wherein the culturing was not conducted in the presence of an OFA epitope that specifically stimulates T suppressor cells.

10. The method of claim 1 or 9, wherein the cancer is a sarcoma.

11. The method of claim 10, wherein the sarcoma is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma and rhabdomyosarcoma.

12. The method of claim 1 or 9, wherein the cancer is a carcinoma.

13. The method of claim 12, wherein the carcinoma is selected from the group consisting of colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma.

14. The method of claim 13, wherein the carcinoma is breast cancer.

15. The method of claim 13, wherein the carcinoma is ovarian cancer.

16. The method of claim 1 or 9, wherein the cancer is a lymphoma.

17. The method of claim 16, wherein the lymphoma is selected from the group consisting of leukemia, lymphoma, polycythemia vera, multiple myeloma, Waldenstrom's macroglobulinemia and heavy chain disease.

18. The method of claim 17, wherein the leukemia is selected from the group consisting of acute lymphocytic leukemia, acute myelocytic leukemia and chronic leukemia.

19. The method of claim 17, wherein the lymphoma is Hodgkin's disease.

20. The method of claim 17, wherein the lymphoma is non-Hodgkin's disease.

\* \* \* \* \*